(12) United States Patent
Ensign et al.

(10) Patent No.: US 9,415,020 B2
(45) Date of Patent: Aug. 16, 2016

(54) NANOPARTICLE FORMULATIONS WITH ENHANCED MUCOSAL PENETRATION

(71) Applicant: The Johns Hopkins University, Baltimore, MD (US)

(72) Inventors: Laura Ensign, Towson, MD (US); Richard Cone, Baltimore, MD (US); Justin Hanes, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/373,324

(22) PCT Filed: Jan. 21, 2013

(86) PCT No.: PCT/US2013/022387
§ 371 (c)(1),
(2) Date: Jul. 18, 2014

(87) PCT Pub. No.: WO2013/110028
PCT Pub. Date: Jul. 25, 2013

(65) Prior Publication Data
US 2015/0297531 A1    Oct. 22, 2015

Related U.S. Application Data

(60) Provisional application No. 61/588,350, filed on Jan. 19, 2012.

(30) Foreign Application Priority Data

Feb. 8, 2012    (WO) ................ PCT/US2012/024344
Dec. 14, 2012   (WO) ................ PCT/US2012/069882

(51) Int. Cl.
*A61K 9/51*     (2006.01)
*A61K 31/704*   (2006.01)
*A61K 9/00*     (2006.01)

(52) U.S. Cl.
CPC ............ *A61K 9/5146* (2013.01); *A61K 9/0031* (2013.01); *A61K 9/0034* (2013.01);
(Continued)

(58) Field of Classification Search
None
See application file for complete search history.

(56) References Cited

U.S. PATENT DOCUMENTS 4,997,652 A    3/1991   Wong
5,034,506 A    7/1991   Summerton
(Continued)

FOREIGN PATENT DOCUMENTS

WO    9207866      5/1992
WO    2006063249   6/2006
(Continued)

OTHER PUBLICATIONS

YY Wang, SK Lai, JS Suk, A Pace, R Cne, J Hanes. "Addressing the PEG Mucoadhesivity Paradox to Engineer Nanoparticles that "Slip" through the Human Mucus Barrier." Angewandte Chemie International Edition, vol. 47, 2008, pp. 9726-9729.*
(Continued)

*Primary Examiner* — Isaac Shomer
(74) *Attorney, Agent, or Firm* — Pabst Patent Group LLP

(57) ABSTRACT

Hypotonic formulations were evaluated for delivering water-soluble drugs and for drug delivery with muco-inert (that is, non-adhesive) mucus-penetrating nanoparticles (MPP). Hypotonic formulations markedly increased the rate at which drugs and MPP reached the epithelial surface, including deep into the vaginal folds. Minimally hypotonic formulations, preferably ranging from 20-220 mOsm/kg, provided rapid and uniform delivery of MPP to the entire vaginal surface, with minimal risk of epithelial toxicity. Data also show that there is a higher osmolality in the colon, such that vehicles with an osmolality above that of blood plasma (generally considered isotonic at ~300 mOsm/kg), still lead to improvements in distribution in the colon due to rapid, osmotically-induced fluid absorption. The range for improved colon distribution with a hypotonic vehicle in the colon is ~20 mOsm/kg-450 mOsm/kg.

21 Claims, 9 Drawing Sheets

(52) U.S. Cl.
CPC ............... *A61K 9/51* (2013.01); *A61K 9/5138* (2013.01); *A61K 9/5153* (2013.01); *A61K 31/704* (2013.01); *Y10S 977/773* (2013.01); *Y10S 977/906* (2013.01)

(56) References Cited

U.S. PATENT DOCUMENTS

| | | | |
|---|---|---|---|
| 5,578,325 | A | 11/1996 | Domb |
| 5,710,135 | A | 1/1998 | Leenders |
| 5,869,130 | A | 2/1999 | Ferrier |
| 5,932,462 | A | 8/1999 | Harris |
| 6,007,845 | A | 12/1999 | Domb |
| 6,287,588 | B1 | 9/2001 | Shih |
| 6,413,539 | B1 | 7/2002 | Shalaby |
| 6,495,164 | B1 | 12/2002 | Ramstack |
| 6,509,323 | B1 | 1/2003 | Davis |
| 6,589,549 | B2 | 7/2003 | Shih |
| 6,706,289 | B2 | 3/2004 | Lewis |
| 8,354,476 | B2 | 1/2013 | Hanes |
| 8,409,607 | B2 | 4/2013 | Hughes |
| 8,465,778 | B2 | 6/2013 | Hughes |
| 8,481,069 | B2 | 7/2013 | Hughes |
| 8,512,738 | B2 | 8/2013 | Edelman |
| 8,628,801 | B2 | 1/2014 | Garreta |
| 8,632,809 | B2 | 1/2014 | Asgharian |
| 8,663,674 | B2 | 3/2014 | Wen |
| 8,911,768 | B2 | 12/2014 | Whitcup |
| 2003/0068277 | A1 | 4/2003 | Vanbever |
| 2003/0180366 | A1* | 9/2003 | Kirschner ............... A61K 47/12 424/489 |
| 2004/0234611 | A1 | 11/2004 | Ahlheim |
| 2005/0009910 | A1 | 1/2005 | Hughes |
| 2005/0176945 | A1* | 8/2005 | Mount, Jr. ............ C07K 14/705 536/23.5 |
| 2006/0276473 | A1* | 12/2006 | Bostion ................. A61K 31/00 514/241 |
| 2007/0071756 | A1 | 3/2007 | Peyman |
| 2007/0149593 | A1 | 6/2007 | Ghosh |
| 2007/0219122 | A1 | 9/2007 | Glazer |
| 2007/0231360 | A1 | 10/2007 | Peyman |
| 2008/0070920 | A1 | 3/2008 | Guo |
| 2008/0086199 | A1 | 4/2008 | Dave |
| 2008/0166411 | A1 | 7/2008 | Shah |
| 2008/0166414 | A1* | 7/2008 | Hanes ................... A61K 9/0073 424/490 |
| 2008/0305172 | A1 | 12/2008 | Ahlheim |
| 2009/0203709 | A1 | 8/2009 | Steinberg |
| 2010/0160252 | A1* | 6/2010 | Chetoni ............... A61K 9/0048 514/54 |
| 2010/0215580 | A1* | 8/2010 | Hanes ................... A61K 9/0034 424/9.1 |
| 2010/0227905 | A1 | 9/2010 | Kabra |
| 2011/0262406 | A1 | 10/2011 | delCampo |
| 2012/0052041 | A1 | 3/2012 | Basu |
| 2012/0157499 | A1 | 6/2012 | Hughes |
| 2012/0269894 | A1 | 10/2012 | Ahlheim |
| 2013/0071349 | A1 | 3/2013 | Robinson |
| 2013/0122064 | A1 | 5/2013 | Ahlheim |
| 2013/0316001 | A1 | 11/2013 | Popov |
| 2013/0316006 | A1 | 11/2013 | Popov |
| 2013/0316009 | A1 | 11/2013 | Popov |
| 2014/0031408 | A1 | 1/2014 | Edelman |
| 2014/0107025 | A1 | 4/2014 | Wirostko |
| 2014/0178475 | A1 | 6/2014 | Figueiredo |
| 2014/0248358 | A1 | 9/2014 | Figueiredo |
| 2014/0249158 | A1 | 9/2014 | Figueiredo |
| 2014/0276482 | A1 | 9/2014 | Astafieva |
| 2014/0294986 | A1 | 10/2014 | Liu |

FOREIGN PATENT DOCUMENTS

| | | |
|---|---|---|
| WO | 2007016380 | 2/2007 |
| WO | 2007084418 | 7/2007 |
| WO | 2010040188 | 4/2010 |
| WO | 2010132664 | 11/2010 |
| WO | 2013166408 | 11/2013 |
| WO | 2013166436 | 11/2013 |
| WO | 2014047439 | 3/2014 |

OTHER PUBLICATIONS

Y-Y Wang, SK Lai, JS Suk, A Pace, R Cone, J Hanes. "Addressing the PEG Mucoadhesivity Paradox to Engineer Nanoparticles that "Slip" through the Human Mucus Barrier." Angewandte Chemie International Edition, vol. 47, 2008, pp. 9726-9729.*

LM Ensign, R Cone, J Hanes. "Oral drug delivery with polymeric nanoparticles: The gastrointestinal mucus barriers." Advanced Drug Delivery Reviews, vol. 64, 2012, pp. 557-570, available online Dec. 24, 2011.*

J Eyles, HO Alpar, WN Field, DA Lewis, M Keswick. "The Transfer of Polystyrene Microspheres from the Gastrointestinal Tract to the Circulation after Oral Administration in the Rat." Journal of Pharmacy and Pharmacology, vol. 47, 1995, pp. 561-565.*

Deosarkar, et al.., "Polymeric particles conjugated with a ligand to VCAM-1 exhibit selective, avid, and focal adhesion to sites of atherosclerosis", Biotech. Bioeng., 101(2):400-7 (2008).

Dong, et al., "Vascular cell-adhesion molecule-1 plays a central role in he proangiogenic effects of oxidative stress", PNAS, 108(35):14614-9 (2011).

Veronese, et al., "PEG-doxorubicin conjugates: influence of polymer structure on drug release, in vitro cytotoxicity, biodistribution, and antitumor activity", Bioconjig Chem.,16(4):775-84 (2005).

Yokoyama, et al., "Characterization and anticancer activity of the micelle-forming polymeric anticancer drug adriamycin-conjugated poly(ethylene glycol)-poly(aspartic acid) block copolymer", Cancer Res., 50:1693-1700 (1990).

Cu, et al., "In vivo distribution of surface-modified PLGA nanoparticles following intravaginal delivery", J Cont. Release, 156(2):257-64 (2011).

Astete and Sabliov, "Synthesis and characterization of PLGA nanoparticles", J Biomater Sci Polymer Ed., 17:247-89 (2006).

Bertschinger, et al., "Disassembly of polyethylenimine-DNA particles in vitro: implications for polyethylenimine-mediated DNA delivery", J Control Release, 116:96-104 (2006).

Clark and Friend, "Pharmacokinetics and Topical Vaginal Effects of Two Tenofovir Gels in Rabbits", AIDS Res Hum Retroviruses, 28(11):1458-66 (2012).

das Neves and Bahia, "Gels as vaginal drug delivery systems", Int J Pharm., 318(1-2):1-14 (2006).

Dunmire and Katz, "Alteration of human sperm kinematics in cervical mucus due to nonoxynol-9", Contraception, 55:209-17 (1997).

Ensign, et al., "Mucus-penetrating nanoparticles for vaginal drug delivery protect against herpes simplex virus", Sci Transl Med., 4(138):138ra79 (2012).

Eyles, et al., "The transfer of polystyrene microspheres from the gastrointestinal tract to the circulation after oral administration in the rat", J Pharm. Pharmacol., 47:561-5 (1995).

Fuchs, et al., "Hyperosmolar sexual lubricant causes epithelial damage in the distal colon: potential implication for HIV transmission", J Infect Dis 195:703-710 (2007).

Gref, et al., "'Stealth' corona-core nanoparticles surface modified by polyethylene glycol (PEG): Influences of the corona (PEG chain length and surface density) and of the core composition on phagocytic uptake and plasma protein adsorption", Colloids Surf Biointerfaces, 18:301-13 (2000).

Jain, "The manufacturing techniques of various drug loaded biodegradable poly(lactide-co-glycolide) (PLGA) devices", Biomaterials, 21(23):2475-90 (2000).

Lacey, et al., "Unacceptable side-effects associated with a hyperosmolar vaginal microbicide in a phase 1 trial", Int J STD AIDS, 21:714-7 (2007).

Lai, et al., "Mucus-penetrating nanopartictles for drug and gene delivery to mucosal tissues", Adv Drug Deliver Rev., 61:158-71 (2009).

Lai, et al., "Rapid transport of large polymeric nanoparticles in fresh undiluted human mucus", PNAS, 104:1482-7 (2007).

(56) References Cited

OTHER PUBLICATIONS

Lemoine, et al., "Mechanism of efficient transfection of the nasal airway epithelium by hypotonic shock", Gene Ther., 12(16):1275-85 (2005).

Lennemas, "Does fluid flow across the intestinal mucosa affect quantitative oral drug absorption? Is it time for a reevaluation?", Pharm Res., 12:1573-82 (1995).

Li, et al., "Microencapsulation by solvent evaporation: state of the art for process engineering approaches", Int. J. Pharm., 363(1-2):26-39 (2008).

Moench, et al., "Microbicide excipients can greatly increase susceptibility to genital herpes transmission in the mouse", BMC Infect Dis., 10:331 (2010).

Mundargi, et al., "Nano/micro technologies for delivering macromolecular therapeutics using poly(D,L-lactide-co-glycolide) and its derivatives", J. Control. Release, 125(3)193-209 (2008).

Nance, et al.,"A dense poly(ethylene glycol) coating improves penetration of large polymeric nanoparticles within brain tissue", Sci Transl Med., 4(149)149ra119 (2012).

Noach, et al., "Effect of anisotonic conditions on the transport of hydrophilic model compounds across monolayers of human colonic cell lines", J Pharmacol Exp Ther., 270:1373-80 (1994).

Owen, et al., "Factors influencing nonoxynol-9 permeation and bioactivity in cervical mucus", J Control Release, 60:23-34 (1999).

Pihl et al., Comparative study of the effect of luminal hypotonicity on mucosal permeability in rat upper gastrointestinal tract\, Acta Physiol., 193:67-78(2008).

Rajapaksa, et al., "Intranasal M cell uptake of nanoparticles is independently influenced by targeting ligands and buffer ionic strength", J Biol Chem., 285:23739-46 (2010).

Rudolph, et al., "Aerosolized nanogram quantities of plasmid DNA mediate highly efficient gene delivery to mouse airway epithelium", Mol Ther., 12:493-501 (2005).

Sheng, et al. "In vitro macrophage uptake and in vivo biodistribution of PLA-PEG nanoparticles loaded with hemoglobin as blood substitutes: effect of PEG content", J Mater Sci Mater Med., 20(9)1881-91 (2009).

Wang, et al., "Addressing the PEG mucoadhesivity paradox to engineer nanoparticles that "slip" through the human mucus barrier", Angew Chem Int Ed Engl., 47:9726-9 (2008).

Zeitlin, et al., "Leakage of three commercial vaginal gels in women", Contraception, 68:139-55 (2003).

* cited by examiner

NANOPARTICLE FORMULATIONS WITH ENHANCED MUCOSAL PENETRATION

CROSS-REFERENCE TO RELATED APPLICATIONS

This application is an application under 35 U.S.C. §371 of PCT application no. PCT/US2013/022387, filed Jan. 21, 2013, which claims benefit of U.S. Provisional Application No. 61/588,350, filed Jan. 19, 2012, and International Applications PCT/US2012/024344 filed in the U.S. Receiving Office on Feb. 8, 2012 and PCT/US/2012/069882 filed in the U.S. Receiving Office on Dec. 14, 2012.

GOVERNMENT RIGHTS

The United States government has certain rights in this invention. This work was supported by National Institutes of Health grants R01HD062844, R33AI079740, R01CA140746) (J.H. and R.C.), the National Science Foundation (L.M.E. and the National Institutes of Health/Microbicide Innovation Program 5R21AI079740.

FIELD OF THE INVENTION

This invention is in the field of nanoparticle formulations, particularly hypotonic nanoparticle formulations that rapidly deliver mucus-penetrating nanoparticles to mucosal covered epithelial surfaces, and methods of making and using thereof.

PRIORITY CLAIMS

U.S. Ser. No. 61/588,350 filed Jan. 19, 2012
PCT/US2012/024344 filed Feb. 8, 2012
PCT/US2012/069882 filed Dec. 14, 2012

BACKGROUND OF THE INVENTION

Localized delivery of therapeutics via biodegradable nanoparticles often provides advantages over systemic drug administration, including reduced systemic side effects and controlled drug levels at target sites. However, controlled drug delivery at mucosal surfaces has been limited by the presence of the protective mucus layer.

Mucus is a viscoelastic gel that coats all exposed epithelial surfaces not covered by skin, such as respiratory, gastrointestinal, nasopharyngeal, and female reproductive tracts, and the surface of eye. Mucus efficiently traps conventional particulate drug delivery systems via steric and/or adhesive interactions. As a result of mucus turnover, most therapeutics delivered locally to mucosal surfaces suffer from poor retention and distribution, which limits their efficacy.

Drug and gene carrying nanoparticles delivered to mucus-covered cells in the eyes, nose, lungs, gastrointestinal tract, and female reproductive tract must achieve uniform distribution in order to maximally treat or protect these surfaces. However, the highly viscoelastic (i.e., viscous and solid-like in nature) and adhesive mucus layer can slow or completely immobilize particles, and thereby prevent them from spreading over the mucosal surface. In addition, some mucosal surfaces, such as those of the mouth, stomach, intestines, colon, and vagina, exhibit highly folded epithelial surfaces that are inaccessible to conventional muco-adhesive particles and also to many small molecule drugs and therapeutics. Without maximal distribution with penetration into these deep recesses, much of the epithelium is left susceptible and/or untreated. Additionally, penetration into the folds, presumably containing a much more slowly cleared mucus layer, allows for increased residence time at the epithelial surface.

For drug or gene delivery applications, therapeutic particles must be able to 1) achieve uniform distribution over the mucosal surface of interest, as well as 2) cross the mucus barrier efficiently to avoid rapid mucus clearance and ensure effective delivery of their therapeutic payload to underlying cells (das Neves J & Bahia M F *Int J Pharm* 318, 1-14 (2006); Lai et al. *Adv Drug Deliver Rev* 61, 158-171 (2009); Ensign et al. *Sci Transl Med* 4, 138ra179 (2012); Eyles et al. *J Pharm Pharmacol* 47, 561-565 (1995)).

Biodegradable nanoparticles that penetrate deep into the mucus barrier can provide improved drug distribution, retention and efficacy at mucosal surfaces. Dense surface coats of low molecular weight polyethylene glycol (PEG) allow nanoparticles to rapidly penetrate through highly viscoelastic human and animal mucus secretions. The hydrophilic and bioinert PEG coating effectively minimizes adhesive interactions between nanoparticles and mucus constituents. Biodegradable mucus-penetrating particles (MPPs) have been prepared by physical adsorption of certain PLURONICs, such as F127, onto pre-fabricated mucoadhesive nanoparticles.

The surface of the vagina is highly folded to accommodate expansion during intercourse and childbirth; these folds, or "rugae," are normally collapsed by intra-abdominal pressure, hindering drug delivery to the folded surfaces. For truly effective prevention and treatment, sustained drug concentrations must be delivered to, and maintained over the entire susceptible surface. Failure to achieve adequate distribution over the entire vaginal epithelium is a documented failure mode of vaginal microbicides.

Another significant barrier to effective drug delivery to the vagina is the viscoelastic layer of mucus secreted by the endocervix that coats the vaginal epithelium. Mucus efficiently traps foreign particles and particulates by both steric and adhesive mechanisms, facilitating rapid clearance. Although the use of mucoadhesive dosage forms has been proposed for increasing residence time in the vagina, mucus clearance occurs rapidly (on the order of minutes to hours), limiting the residence time of mucoadhesive systems.

Mucosal epithelia use osmotic gradients to cause fluid absorption and secretion. Vaginal products have traditionally been made with hypertonic formulations, including yeast infection treatments, most sexual lubricants such as KY® warming gel, and gels designed for preventing sexually transmitted infections such as HIV. Hypertonic formulations cause rapid, osmotically-driven secretion of fluid into the vagina, and this causes an immediate increase in fluid leakage from the vagina at a rate proportional to the hypertonicity of the formulation. Moreover, recent investigations of candidate vaginal and rectal microbicides both in animal models and in humans have revealed that hypertonic formulations cause toxic effects that can increase susceptibility to infections. The first successful microbicide trial for HIV prevention found that the antiretroviral drug, tenofovir, delivered in a vaginal gel, provided partial protection. Unfortunately, the gel formulation was highly hypertonic, leading investigators in the most recent clinical trial of tenofovir to reduce the concentration of glycerol to reduce toxicity. However, the concentration was not reduced, and the formulation is still significantly hypertonic. There appears to be no evidence to justify hypertonic formulations for vaginal drug delivery, since in addition to the documented toxic effects, hypertonic formulations cause rapid osmotically-driven secretion of vaginal fluid, fluid flow that opposes the delivery of drugs to the epithelium. This lack of justification has been ignored by both investigators and manufacturers of vaginal products, the only evident exception being sexual lubricants intended to support fertilization. These products are formulated to be isotonic (the osmolality is equivalent to that of plasma) to help maintain viability of sperm.

Therefore, it is an object of the invention to provide formulations for rapid and uniform particulate delivery of a wide range of drugs to mucosal covered epithelial surfaces with minimal toxicity to the epithelium.

SUMMARY OF THE INVENTION

Osmosis can be used to cause rapid penetration of mucus-penetrating particles into deep recesses in highly-folded mucosal tissues. Absorption and penetrability into the deep recesses of mucosal tissues improves the distribution over a mucosal surface of otherwise poorly distributed entities. Rapid absorption and penetrability into deep recesses of mucosal tissues leads to increased residence time of mucus-penetrating particles. Rapid absorption facilitates user acceptability in addition to increasing the effectiveness of the treatment and minimizing the time between application and mucosal protection.

Hypotonic formulations were evaluated for delivering water-soluble drugs and for drug delivery with muco-inert (that is, non-adhesive) mucus-penetrating nanoparticles (MPP). Hypotonic formulations markedly increased the rate at which drugs and MPP reached the epithelial surface. Additionally, hypotonic formulations greatly enhanced drug and MPP delivery to the entire epithelial surface, including deep into the vaginal folds (rugae) that isotonic formulations failed to reach. Hypotonic formulations can cause free drugs not only to be drawn to the epithelium but also be drawn through the epithelium, reducing vaginal retention. In contrast, hypotonic formulations cause MPP to accumulate rapidly and uniformly on vaginal surfaces, but they do not pass through the epithelium and thus remain ideally positioned for sustained mucosal drug delivery. Minimally hypotonic formulations, preferably ranging from 20-220 mOsm/kg, provided rapid and uniform delivery of MPP to the entire vaginal surface, with minimal risk of epithelial toxicity. Hypotonic formulations for vaginal drug delivery via MPP should significantly improve prevention and treatment of reproductive tract diseases and disorders.

Data also show that there is a higher osmolality in the colon, such that vehicles with an osmolality above that of blood plasma (generally considered isotonic at ~300 mOsm/kg), still lead to improvements in distribution in the colon due to rapid, osmotically-induced fluid absorption. The range for improved colon distribution with a hypotonic vehicle in the colon is ~20 mOsm/kg-450 mOsm/kg. In the preferred embodiment, the formulation for application to the colon or rectum has an osmolality between about 20 mOsm/kg and 450 mOsm/kg, wherein sodium ions ($Na^+$) cause at least 30% of the osmolality in excess of 220 mOsm/kg. (i.e., if the osmolality of the formulation is 450 mOsm/kg, $Na^+$ ions must comprise at least 30% to 450-220=230 mOsm/kg, or 69 mOsm/kg). Improved distribution of hypotonically administered MPP (compared to CP) on rectal tissue with induced ulcerative colitis, including uptake of MPP into the ulcerated tissue, was also demonstrated. Hypotonic administration also leads to improved distribution of free drug (tenofovir labeled with FITC) in the colon.

BRIEF DESCRIPTION OF THE DRAWINGS

FIG. 2a is a graph showing the ensemble-averaged geometric mean square displacement <MSD/$\mu m^2$> as a function of time scale/s. FIG. 2b is a graph showing the distributions of the logarithms of individual particle effective diffusivities ($D_{eff}$) at a time scale of 1 s. Particles were prepared with the emulsification method using PLGA-PEG (6 wt % PEG). Data represent three independent experiments with ≥120 nanoparticles tracked for each experiment. Error bars are presented as s.e.m.

FIGS. 4a-c shows the preparation of PLGA-PEG nanoparticles with surface PEG coating at increasing coverage. As surface PEG coverage increases, PEG regime changes from mushroom (neighboring PEG chains do not overlap, [Γ/Γ*]<1, FIG. 4a), to brush (neighboring PEG chains overlap, 1<[Γ/Γ*]<3, FIG. 4b), to dense brush ([Γ/Γ*] >3, FIG. 4c). At low PEG coverage ([Γ/Γ*]<1, FIG. 4a), mucin fibers strongly adhere to nanoparticle core. At middle PEG coverage (1<[Γ/Γ/]<3, FIG. 4b), mucin fibers still can partially absorb to the nanoparticle core. At high ([Γ/Γ*]>3, FIG. 4c) PEG coverage, the nanoparticle cores were completely shielded by the bioinert PEG corona resulting in no adsorption of mucin to nanoparticles. FIG. 4c shows that nanoparticles with low PEG coverage are immobilized in mucus, nanoparticles with middle PEG coverage are hindered or even immobilized in mucus, and nanoparticles with high and very high PEG coverage are able to rapidly penetrate mucus.

FIG. 8A, mice remained supine for 1 hr prior to tissue collection (non-ambulatory). FIG. 8B, mice were ambulatory for 10 minutes prior to tissue collection (ambulatory). Particle retention was calculated as mean±SEM (n≥5). *P<0.05 as compared to isotonic, Wilcoxon rank-sum test.

DETAILED DESCRIPTION OF THE INVENTION

Figure 1A:
FIGS. 1a and 1b are representative trajectories of PLA-PEG and PCL-PEG nanoparticles containing CHA and PVA prepared by an emulsification method.

Many mucosal surfaces, such as those of the mouth, stomach, intestines, colon, and vagina, contain numerous deep epithelial folds to accommodate expansion of the epithelium and absorption of fluids and nutrients. For these reasons, a significant portion of the epithelial surface is contained in these hard to access folds. The ability to engineer particles that uniformly distribute on mucosal tissue surfaces holds many important implications for therapeutics delivery, imaging, and diagnostic applications. For example, particles that do not achieve uniform distribution and penetrate into the deep recesses fail to completely treat or protect a mucosal surface (Rajapaksa et al. *J Biol Chem* 285, 23739-23746 (2010).

In the field of vaginal drug delivery, achieving adequate distribution to all target surfaces is an often-cited problem. The vaginal surface is highly folded to accommodate expansion during intercourse and childbirth, resulting in collapsed folds, or "rugae." Poor distribution into the rugae, even after simulated intercourse, has been cited as a critical factor in the failure of microbicide products to protect against vaginal infection. Other microbicide studies in mice have used large volumes of test product (up to 40 µl), to promote more complete vaginal distribution. The mouse vagina can hold a volume of ~50 µl; such a comparatively large volume of test agent distends and unfolds the vaginal epithelium. In contrast, the human vagina can retain in the range of 50 ml, while typical vaginal products deliver only 2-5 ml. To investigate vaginal distribution in mice in vivo, a small volume (5 µl) that would more appropriately mimic the volumes used in humans was used. A method that delivers drugs into the deep folded surfaces, without distending the vagina, could lead to more effective vaginal drug delivery.

The vaginal epithelium is permeable to small molecules, and capable of absorbing various drugs. The superficial layer of the vaginal epithelium contains densely packed dead and dying cells (the stratum corneum) that protects the deeper living cell layers while allowing secretion and absorption of fluid through the epithelium. The vagina has a native capacity for osmotically-induced fluid absorption that can be used for drug delivery. Doxorubicin administered in hypotonic solution coated more than 85% of the vaginal surface of ambulatory mice, whereas only 25% of the vaginal tissue surface was coated with Doxorubicin administered in isotonic solution. The isotonic fluid does not penetrate into the rugae, leaving a striping pattern when the vaginal tissue is flattened. It has been suggested that hypotonic delivery could increase the contraceptive efficacy of the detergent nonoxynol-9 (N9) by improving mobility of N9 through mucus (Dunmire E N & Katz D F *Contraception* 55, 209-217 (1997); Owen et al. *J Control Release* 60, 23-34 (1999)). Enhanced penetration of hypotonic N9 solution though mucus was shown in isolated mucus in vitro, the focus being to achieve more rapid contact between the detergent and sperm in the mucus.

Delivery to the cervicovaginal tract and colon in particular can be challenging not only because of distribution issues, but also because of "leakage". Most vaginal and rectal formulations are highly hyperosmolar, which causes fluid to be osmotically secreted from the mucosal epithelium. This fluid secretion leads to dilution and leakage of the formulation, along with toxicity associated with the hyperosmolarity (Rudolph et al. *Mol Ther* 12, 493-501 (2005); Bertschinger et al. *Journal of Controlled Release* 116, 96-104 (2006); Pihl et al *Acta Physiol* 193, 67-78 (2008); Noach *J Pharmacol Exp Ther* 270, 1373-1380 (1994)). Drug absorption using hypotonic drug solutions is known but not the effects of absorption on distribution and retention. See, for example, Eyles et al. *J Pharm Pharmacol* 47, 561-565 (1995); Rajapaksa et al. *J Biol Chem* 285, 23739-23746 (2010); Rudolph et al. *Mol Ther* 12, 493-501 (2005); Bertschinger et al. *Journal of Controlled Release* 116, 96-104 (2006); Pihl et al. *Acta Physiol* 193, 67-78 (2008); Noach et al. *J Pharmacol Exp Ther* 270, 1373-1380 (1994); Lennernas H *Pharmaceut Res* 12, 1573-1582 (1995).

Tonicity of a formulation depends on the permeability properties of the tissue (colon versus vaginal, for example) and there is a critical mildly hypotonic range for increased uptake and uniformity of distribution without toxicity. Mildly hypotonic formulations should cause fluid absorption, which would decrease the "leakage" often reported as an adverse side effect by patients in clinical trials. This leaking of product leads to both decreased user acceptability, as well as rapid removal of the therapeutic agent. For example, a reduction in osmolality from 294 mOsm/kg to 220 mOsm/kg acted as a mildly hypotonic fluid that increased vaginal surface coverage from 60% to 76%, and essentially all hypotonically delivered MPP were drawn from the lumen to reach the epithelial surface deep within folded surfaces within 10 min of administration.

Particulate formulations that rapidly achieve uniform distribution, as well as transport through mucus, can be used to efficiently target mucus-covered epithelia in the body for a wide spectrum of applications, including drug therapies (ranging from small molecule therapeutics like chemotherapeutics, to peptides, proteins, oligonucleotoides, DNA, etc.), imaging, and diagnostics. For therapeutic purposes, molecules entrapped in the particles can then be released over prolonged times at predetermined rates. In general, therapeutic applications for the technology include the delivery of any drug where a standard formulation is not feasible, is not 100% effective, or leads to unwanted side-effects due to inefficient distribution, toxicity, or "leakage". The method should also improve penetration and uniform distribution of standard drug formulations (i.e., without drug delivery particles), specifically for gene/oligonucleotide delivery; targeted and highly localized chemotherapy delivery to treat cancer; targeted delivery of anti-inflammation drugs; treatment or prevention of STDs; penetration into biofilms and other biological coatings/barriers; and targeted delivery of antibiotics to treat bacterial infections.

Most vaginal gels have been formulated with excipients such as glycerin or propylene glycol that render the gels hypertonic. Unfortunately, recent investigations show that these hypertonic formulations cause toxicity in the vaginal tract of mice that increases susceptibility to HSV-2 infection (Moench et al. *BMC Infect Dis* 10, 331 (2010)), which is likely by being hypertonic (Fuchs et al. *J Infect Dis* 195, 703-710 (2007); Clark M R & Friend D R (2012) Pharmacokinetics and Topical Vaginal Effects of Two Tenofovir Gels in Rabbits. *AIDS Res Hum Retroviruses*). In addition a hypertonic gel formulation was found to disrupt epithelial integrity in the human colon, and a hypertonic tenofovir gel formulation was found to induce epithelial fracture in ectocervical and colorectal explants compared with tissues exposed to medium only (Rohan *PLoS One* 5, e9310 (2010)). It has been postulated that a major contributing factor in the dextran sodium sulfate (DSS)-induced experimental irritable bowel disease mouse model is the hypertonicity of the DSS solution. Inflammatory cytokine release in mouse vaginal lavage fluid was increased after 7 once-daily doses of a hypertonic gel vehicle, but no increase after 7 once-daily doses of a hypotonic formulation.

I. DEFINITIONS

"Nanoparticle," as used herein, generally refers to a particle of any shape having a diameter from about 1 nm up to, but not including, about 1 micron, more preferably from about 5 nm to about 500 nm, most preferably from about 5 nm to about 100 nm. Nanoparticles having a spherical shape are generally referred to as "nanospheres".

"Mean particle size," as used herein, generally refers to the statistical mean particle size (diameter) of the particles in a population of particles. The diameter of an essentially spherical particle may be referred to as the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution," are used interchangeably herein and describe a plurality of nanoparticles or microparticles where the particles have the same or nearly the same diameter or aerodynamic diameter. As used herein, a monodisperse distribution refers to particle distributions in which 80, 81, 82, 83, 84, 85, 86, 86, 88, 89, 90, 91, 92, 93, 94, 95% or greater of the distribution lies within 5% of the mass median diameter or aerodynamic diameter.

"Hydrophilic" as used herein refers to substances that have strongly polar groups that readily interact with water.

"Lipophilic" refers to compounds having an affinity for lipids.

"Amphiphilic" refers to a molecule combining hydrophilic and lipophilic (hydrophobic) properties "Hydrophobic" as used herein refers to substances that lack an affinity for water; tending to repel and not absorb water as well as not dissolve in or mix with water.

"Pharmaceutically acceptable" as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

"Biocompatible" and "biologically compatible," as used herein, generally refer to materials that are, along with any metabolites or degradation products thereof, generally nontoxic to the recipient, and do not cause any significant adverse effects to the recipient. Generally speaking, biocompatible materials are materials which do not elicit a significant inflammatory or immune response when administered to a patient.

"Molecular weight," as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Hydrophilic," as used herein, refers to the property of having affinity for water. For example, hydrophilic polymers (or hydrophilic polymer segments) are polymers (or polymer segments) which are primarily soluble in aqueous solutions and/or have a tendency to absorb water. In general, the more hydrophilic a polymer is, the more that polymer tends to dissolve in, mix with, or be wetted by water.

"Hydrophobic," as used herein, refers to the property of lacking affinity for, or even repelling water. For example, the more hydrophobic a polymer (or polymer segment), the more that polymer (or polymer segment) tends to not dissolve in, not mix with, or not be wetted by water.

"Mucus," as used herein, refers to a viscoelastic natural substance containing primarily mucin glycoproteins and other materials, which protects epithelial surface of various organs/tissues, including respiratory, nasal, cervicovaginal, gastrointestinal, rectal, visual and auditory systems. "Sputum," as used herein, refers to highly viscoelastic mucus secretions consist of a variety of macromolecules such as DNA, actins and other cell debris released from dead cells in addition to mucin glycoproteins. "Sputum" is generally present in the pathogenic airways of patients afflicted by obstructive lung diseases, including but not limited to, asthma, COPD and CF. "CF mucus" and "CF sputum," as used herein, refer to mucus and sputum, respectively, from a patient suffering from cystic fibrosis.

"Mucus Degrading Agent," as used herein, refers to a substance which increases the rate of mucus clearance when administered to a patient. Mucus degrading agents are known in the art. See, for example, Hanes, J. et al, *Gene Delivery to the Lung.* in *Pharmaceutical Inhalation Aerosol Technology*, Marcel Dekker, Inc., New York: 489-539 (2003). Examples of mucus degrading agents include N-acetylcysteine (NAC), which cleaves disulfide and sulfhydryl bonds present in mucin. Other mucus degrading agents include mugwort, bromelain, papain, clerodendrum, acetylcysteine, bromhexine, carbocisteine, eprazinone, mesna, ambroxol, sobrerol, domiodol, denufosol, letosteine, stepronin, tiopronin, gelsolin, thymosin 134, neltenexine, erdosteine, and various DNases including rhDNase.

The term "surfactant" as used herein refers to an agent that lowers the surface tension of a liquid.

The term "therapeutic agent" refers to an agent that can be administered to prevent or treat a disease or disorder. Therapeutic agents can be a nucleic acid, a nucleic acid analog, a small molecule, a peptidomimetic, a protein, peptide, carbohydrate or sugar, lipid, or surfactant, or a combination thereof.

The term "treating" or preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The term "targeting moiety" as used herein refers to a moiety that localizes to or away from a specific locale. The moiety may be, for example, a protein, nucleic acid, nucleic acid analog, carbohydrate, or small molecule. The entity may be, for example, a therapeutic compound such as a small molecule, or a diagnostic entity such as a detectable label. The locale may be a tissue, a particular cell type, or a subcellular compartment. In one embodiment, the targeting moiety directs the localization of an active entity. The active entity may be a small molecule, protein, polymer, or metal. The active entity may be useful for therapeutic, prophylactic, or diagnostic purposes.

The term "therapeutically effective amount" refers to an amount of the therapeutic agent that, when incorporated into and/or onto particles described herein, produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

The terms "incorporated" and "encapsulated" refers to incorporating, formulating, or otherwise including an active agent into and/or onto a composition that allows for release, such as sustained release, of such agent in the desired application. The terms contemplate any manner by which a therapeutic agent or other material is incorporated into a polymer matrix, including, for example: attached to a monomer of such polymer (by covalent, ionic, or other binding interaction), physical admixture, enveloping the agent in a coating layer of polymer, incorporated into the polymer, distributed throughout the polymeric matrix, appended to the surface of the polymeric matrix (by covalent or other binding interactions), encapsulated inside the polymeric matrix, etc. The tens "co-incorporation" or "co-encapsulation" refers to-the incorporation of a therapeutic agent or other material and at least one other therapeutic agent or other material in a subject composition.

Conventional use of the term "isotonic" refers to fluids that do not cause cells to swell or shrink, which typically occurs when the total solute concentrations (osmolality) is equal to that of the blood (~300 mOsm/kg). Isotonic is defined herein as a formulation that does not cause water to enter or leave the lumen or be driven osmotically through the epitheliuim. Hypotonic is defined herein to refer to formulations that cause water to flow inward, toward the epithelium from the mucosal surface, and hypertonic formulations are defined as those that cause water to flow outward, toward the mucus-coated surface.

"Mucus-penetrating particle" or "MPP", as used herein, generally refers to particles which have been coated with a mucosal penetration enhancing coating. In some embodiments, the particles are particles of an active agent, such as a therapeutic, diagnostic, prophylactic, and/or nutraceutical agent (i.e., drug particle) that is coated with a mucosal penetrating enhancing coating as described below. In other embodiments, the particles are formed of a matrix material, such as a polymeric material, in which the therapeutic, diagnostic, prophylactic, and/or nutraceutical agent is encapsulated, dispersed, and/or associated. The coating material can be covalently or non-covalently associated with the drug particle or polymeric particle

II. MUCUS-PENETRATING NANOPARTICLES (MPPs)

A. Polymeric Particles

1. Core Polymer

Any number of biocompatible polymers can be used to prepare the nanoparticles. In one embodiment, the biocompatible polymer(s) is biodegradable. In another embodiment, the particles are non-degradable. In other embodiments, the particles are a mixture of degradable and non-degradable particles.

Exemplary polymers include, but are not limited to, cyclodextrin-containing polymers, in particular cationic cyclodextrin-containing polymers, such as those described in U.S. Pat. No. 6,509,323; polymers prepared from lactones, such as poly(caprolactone) (PCL); polyhydroxy acids and copolymers thereof such as poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(D,L-lactide-co-caprolactone), poly(D,L-Iactide-co-caprolactone-co-glycolide), poly(D,L-lactide-co-PEO-co-D,L-lactide), poly(D,L-lactide-co-PPO-co-D,L-lactide), and blends thereof, polyalkyl cyanoacralate, polyurethanes, polyamino acids such as poly-L-lysine (PLL), poly(valeric acid), and poly-L-glutamic acid; hydroxypropyl methacrylate (HPMA); polyanhydrides; polyesters; polyorthoesters; poly (ester amides); polyamides; poly(ester ethers); polycarbonates; polyalkylenes such as polyethylene and polypropylene; polyalkylene glycols such as poly(ethylene glycol) (PEG) and polyalkylene oxides (PEO), and block copolymers thereof such as polyoxyalkylene oxide ("PLURONICS®"); polyalkylene terephthalates such as poly(ethylene terephthalate); ethylene vinyl acetate polymer (EVA); polyvinyl alcohols (PVA); polyvinyl ethers; polyvinyl esters such as poly (vinyl acetate); polyvinyl halides such as poly(vinyl chloride) (PVC), polyvinylpyrrolidone; polysiloxanes; polystyrene (PS; celluloses including derivatized celluloses such as alkyl celluloses, hydroxyalkyl celluloses, cellulose ethers, cellulose esters, nitro celluloses, hydroxypropylcellulose, and carboxymethylcellulose; polymers of acrylic acids, such as poly (methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) (jointly referred to herein as "polyacrylic acids"); polydioxanone and its copolymers; polyhydroxyalkanoates; polypropylene fumarate; polyoxymethylene; poloxamers; poly(butyric acid); trimethylene carbonate; and polyphosphazenes. Examples of preferred natural polymers include proteins such as albumin, collagen, gelatin and prolamines, for example, zein, and polysaccharides such as alginate. Copolymers of the above, such as random, block, or graft copolymers, or blends of the polymers listed above can also be used.

Functional groups on the polymer can be capped to alter the properties of the polymer and/or modify (e.g., decrease or increase) the reactivity of the functional group. For example, the carboxyl termini of carboxylic acid contain polymers, such as lactide- and glycolide-containing polymers, may optionally be capped, e.g., by esterification, and the hydroxyl termini may optionally be capped, e.g. by etherification or esterification.

Copolymers of PEG or derivatives thereof with any of the polymers described above may be used to make the polymeric particles. In certain embodiments, the PEG or derivatives may be located in the interior positions of the copolymer. Alternatively, the PEG or derivatives may locate near or at the terminal positions of the copolymer. For example, one or more of the polymers above can be terminated with a block of polyethylene glycol. In some embodiments, the core polymer is a blend of pegylated polymer and non-pegylated polymer, wherein the base polymer is the same (e.g., PLGA and PLGA-PEG) or different (e.g., PLGA-PEG and PLA). In certain embodiments, the microparticles or nanoparticles are formed under conditions that allow regions of PEG to phase separate or otherwise locate to the surface of the particles. The surface-localized PEG regions alone may perform the function of, or include, the surface-altering agent. In particular embodiments, the particles are prepared from one or more polymers terminated with blocks of polyethylene glycol as the surface-altering material.

The weight average molecular weight can vary for a given polymer but is generally from about 1000 Daltons to 1,000,000 Daltons, 1000 Daltons to 500,000 Dalton, 1000 Daltons to 250,000 Daltons, 1000 Daltons to 100,000 Daltons, 5,000 Daltons to 100,000 Daltons, 5,000 Daltons to 75,000 Daltons, 5,000 Daltons to 50,000 Daltons, or 5,000 Daltons to 25,000 Daltons.

In some embodiments, the particles may be used as nanoparticle gene carriers. In these embodiments, the particles can be formed of one or more polycationic polymers which complex with one or more nucleic acids which are negatively charged. The cationic polymer can be any synthetic or natural polymer bearing at least two positive charges per molecule and having sufficient charge density and molecular size to bind to nucleic acid under physiological conditions (i.e., pH and salt conditions encountered within the body or within cells). In certain embodiments, the polycationic polymer contains one or more amine residues.

B. Coated Drug Particles

In some embodiments, the particles of the therapeutic, diagnostic, prophylactic, and/or nutriceutical agent is coated with mucosal penetration enhancing coating. The particle can be microparticles or nanoparticles. Exemplary therapeutic, diagnostic, prophylactic, and/or nutriceutical agents are described in more detail below. The drug particles can be coated with mucosal penetration enhancing coating materials using techniques known in the art. The density and morphology of the coating can be evaluated as described below. The mucosal penetration enhancing coating can be covalently or non-covalently associated with the agent. In some embodiments, it is non-covalently associated. In other embodiments, the active agent contains a reactive functional group or one is incorporated to which the mucosal penetration enhancing coating can be covalently bound.

C. Materials that Promote Diffusion Through Mucus

The micro- and/or nanoparticles preferably are coated with or contain one or more surface altering agents or materials. "Surface-alternating agents", as used herein refers to an agent or material which modifies one or more properties of the particles for the surface, including, but not limited to, hydrophilicity (e.g., makes the particles more or less hydrophilic), surface charge (e.g., makes the surface neutral or near neutral or more negative or positive), and/or enhances transport in or through bodily fluids and/or tissues, such as mucus. In some embodiments, the surface-alternating material provides a direct therapeutic effect, such as reducing inflammation.

Examples of the surface-altering agents include, but are not limited to, proteins, including anionic proteins (e.g., albumin), surfactants, sugars or sugar derivatives (e.g., cyclodextrin), therapeutics agents, and polymers. Preferred polymers include heparin, polyethylene glycol ("PEG") and poloxomers (polyethylene oxide block copolymers). The most preferred material is PEG or PLURONIC F127®, a polyethylene oxide block copolymer available from BASF.

Examples of surfactants include, but are not limited to, L-α-phosphatidylcholine (PC), 1,2-dipalmitoylphosphatidycholine (DPPC), oleic acid, sorbitan trioleate, sorbitan monooleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil, lecithin, oleic acid, and sorbitan trioleate.

In one embodiment, the particles are coated with or contain polyethylene glycol (PEG) or F127. Alternatively, the PEG or F127 can be in the form of blocks covalently bound (e.g., in the interior or at one or both terminals) to the core polymer used to form the particles. In particular embodiments, the particles are formed from block copolymers containing PEG. In more particular embodiments, the particles are prepared from block copolymers containing PEG, wherein PEG is covalently bound to the terminal of the base polymer. Representative PEG molecular weights include 300 Da, 600 Da, 1 kDa, 2 kDa, 3 kDa, 4 kDa, 6 kDa, 8 kDa, 10 kDa, 15 kDa, 20 kDa, 30 kDa, 50 kDa, 100 kDa, 200 kDa, 500 kDa, and 1 MDa and all values within the range of 300 Daltons to 1 MDa. In preferred embodiments, the PEG has a molecular weight of about 5 kD. PEG of any given molecular weight may vary in other characteristics such as length, density, and branching.

1. Evaluating Surface Density

Surface density of poly(ethylene glycol) (PEG) on microparticles and/or nanoparticles is a key parameter in determining their successful applications in-vivo. (As used herein, general references to PEG on the surface of particles is extrapolatable to PLURONIC® F127. The controlled delivery of drugs to mucosal surfaces is challenging because of the presence of the protective mucus layer, and the mucus-penetrating particles show promise at improved drug distribution, retention and efficacy at mucosal surfaces. The dense coating of PEG on biodegradable nanoparticles can allow rapid penetration through mucus because of the greatly reduced adhesive interaction between mucus constituents and nanoparticles.

In a preferred embodiment, nuclear magnetic resonance (NMR) is used to assess the surface PEG density on PEG-containing polymeric nanoparticles described herein, both qualitatively and quantitatively (PEG peak typically observed ~3.65 ppm). When nanoparticles are dispersed within the NMR solvent $D_2O$, only the surface PEG, not the PEG embedded within the core, can be directly detected by NMR. Therefore, NMR provides a means for directly measure the surface density of PEG.

In some embodiments, PEG surface density can be controlled by preparing the particles from a mixture of pegylated and non-pegylated particles. For example, the surface density of PEG on PLGA nanoparticles can be precisely controlled by preparing particles from a mixture of poly(lactic-co-glycolic acid) and poly(ethylene glycol) (PLGA-PEG). Quantitative $^1H$ nuclear magnetic resonance (NMR) can be used to measure the surface PEG density on nanoparticles. Multiple particle tracking in human mucus and the study of mucin binding and tissue distribution in mouse vagina revealed that there exists a PEG density threshold, which is approximately, 10-16 PEG chains/100 $nm^2$, for PLGA-PEG nanoparticles to be effective in penetrating mucus. This density threshold may vary depending on a variety of factors including the core polymer used to prepare the particles, particle size, and/or molecular weight of PEG.

The density of the coating can be varied based on a variety of factors including the surface altering material and the composition of the particle. In one embodiment, the density of the surface altering material, such as PEG, as measured by H NMR is at least, 0.1, 0.2, 0.5, 0.8, 1, 2, 5, 8, 10, 15, 20, 25, 40, 50, 60, 75, 80, 90, or 100 chains per $nm^2$. The range above is inclusive of all values from 0.1 to 100 units per $nm^2$. In particular embodiments, the density of the surface altering material, such as PEG, is from about 1 to about 25 chains/$nm^2$, from about 1 to about 20 chains/$nm^2$, from about 5 to about 20 chains/$nm^2$, from about 5 to about 18 chains/$nm^2$, from about 5 to about 15 chains/$nm^2$, or from about 10 to about 15 chains/$nm^2$. In other particular embodiments, the density is from about 0.05 to about 0.5 PEG chains/$nm^2$.

The concentration of the surface altering material, such as PEG, can also be varied. In particular embodiments, the density of the surface-altering material (e.g., PEG) is such that the surface-altering material (e.g. PEG) adopted an extended brush configuration. In other embodiments, the mass of the surface-altering moiety is at least 1/10,000, 1/7500, 1/5000, 1/4000, 1/3400, 1/2500, 1/2000, 1/1500, 1/1000, 1/750, 1/500, 1/250, 1/200, 1/150, 1/100, 1/75, 1/50, 1/25, 1/20, 1/5, 1/2, or 9/10 of the mass of the particle. The range above is inclusive of all vales from 1/10,000 to 9/10.

D. Emulsifier

The particles described herein can contain an emulsifier, particularly a low molecular weight emulsifier. The emulsifier is incorporated into the particle during particle formation and therefore is a component of the finished particle. The emulsifier can be encapsulated within the particle, be dispersed in whole or in part within the polymer matrix (e.g., part of the emulsifier extends out from the polymer matrix), and/or is associated (e.g., covalently or non-covalently) with the surface of the particle.

"Low molecular weight", as used herein, generally refers to an emulsifier having a molecular weight less than 1500, 1400, 1300, 1200, 1100, 1000, 900, 800, 700, 600, 500, 400, or 300 amu. In some embodiments, the molecular weight is less than 1300 amu. In some embodiments, the molecular weight is from about 300 amu to about 1200 amu.

The emulsifier can be positively charged, negatively charged, or neutral. Examples of negatively charged emulsifiers include, but are not limited to, cholic acid sodium salt (CHA, MW=430) and dioctyl sulfosuccinate sodium (DSS, MW=455). Examples of positively charged emulsifiers include, but are not limited to, hexadecyltrimethyl ammonium bromide (CTAB, MW=364). Examples of neutral emulsifiers include, but are not limited to, sapon (MW=1191), TWEEN 20 (MW=1,225), TWEEN 80 (MW=1310), and sugar ester D1216 (sucrose laurate, SE, MW=524). In addition to having a low molecular weight, the emulsifier must be capable of suitably stabilizing the emulsion droplets during particle formation in order to prevent particle aggregation. In addition to suitably stabilizing the emulsion droplets to prevent aggregate formation, the stabilizer must be small enough to be completely shielded at the particle surface by the surface altering material corona (e.g., PEG) to provide a neutral or near neutral surface charge. The transport of charged particles may be hindered due to the interaction of the charged particles with oppositely charged species in vivo. For example, the ability of the particles to penetrate mucus rapidly is dependent, at least in part, on the surface charge of the particles. In order to facilitate their diffusion through mucus, the nanoparticles described herein typically possess a near neutral surface charge. In certain embodiments, the nanoparticle possess a ζ-potential of between about 10 mV and about −10 mV, preferably between about 5 mV and about −5 mV, preferably between about 3 mV and about −3 mV, more preferably between about 2 mV and about −2 mV.

While the particles described herein are referred to as nanoparticles, and thus typically have an average diameter in the range of 1 nm up to, but not including, about 1 micron, more preferably from about 5 nm to about 500 nm, most preferably from about 5 nm to about 100 nm. In certain embodiments, the average diameter of the particles is form about 100 nm to about 150 nm. However, particles can be prepared that are sized in the micron-range. The conditions and/or materials used to prepare the particles can be varied to vary the size of the particles.

In certain embodiments, the nanoparticles retain their particle size and ζ-potential after nebulization or storage for at least 1 month, more preferably at least 2 months, most preferably at least 3 months at 4° C.

2. Effect of Emulsifier on Transport Ability

In some embodiments, the particles are administered to penetrate to the mucus for drug delivery to the mucosa. The particles described herein contain a surface-altering material which can enhance transport through the mucus. For example, PEG-containing block copolymers can self-assemble to form dense, muco-inert PEG coatings on the surface of emulsion droplets formed by the emulsification method.

E. Therapeutic, Prophylactic, Nutraceutical and/or Diagnostic Agent

1. Therapeutic Agents

In some embodiments, the particles have encapsulated therein, dispersed therein, and/or covalently or non-covalently associate with the surface one or more therapeutic agents. The therapeutic agent can be a small molecule, protein, polysaccharide or saccharide, nucleic acid molecule and/or lipid.

i. Small Molecule Therapeutic Agents

Exemplary classes of small molecule therapeutic agents include, but are not limited to, analgesics, anti-inflammatory drugs, antipyretics, antidepressants, antiepileptics, antipsychotic agents, neuroprotective agents, anti-proliferatives, such as anti-cancer agent, anti-infectious agents, such as antibacterial agents and antifungal agents, antihistamines, antimigraine drugs, antimuscarinics, anxioltyics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. Nutraceuticals can also be incorporated. These may be vitamins, supplements such as calcium or biotin, or natural ingredients such as plant extracts or phytohormones.

Nucleic Acids

In some embodiments, the agent is one or more nucleic acids. The nucleic acid can alter, correct, or replace an endogenous nucleic acid sequence The nucleic acid is used to treat cancers, correct defects in genes in other pulmonary diseases and metabolic diseases affecting lung function, genes such as those for the treatment of Parkinsons and ALS where the genes reach the brain through nasal delivery.

Gene therapy is a technique for correcting defective genes responsible for disease development. Researchers may use one of several approaches for correcting faulty genes: A normal gene may be inserted into a nonspecific location within the genome to replace a nonfunctional gene. An abnormal gene can be swapped for a normal gene through homologous recombination. The abnormal gene can be repaired through selective reverse mutation, which returns the gene to its normal function. The regulation (the degree to which a gene is turned on or off) of a particular gene can be altered.

The nucleic acid can be a DNA, RNA, a chemically modified nucleic acid, or combinations thereof. For example, methods for increasing stability of nucleic acid half-life and resistance to enzymatic cleavage are known in the art, and can include one or more modifications or substitutions to the nucleobases, sugars, or linkages of the polynucleotide. The nucleic acid can be custom synthesized to contain properties that are tailored to fit a desired use. Common modifications include, but are not limited to use of locked nucleic acids (LNAs), unlocked nucleic acids (UNAs), morpholinos, peptide nucleic acids (PNA), phosphorothioate linkages, phosphonoacetate linkages, propyne analogs, 2'-O-methyl RNA, 5-Me-dC, 2'-5' linked phosphodiester linage, Chimeric Linkages (Mixed phosphorothioate and phosphodiester linkages and modifications), conjugation with lipid and peptides, and combinations thereof.

In some embodiments, the nucleic acid includes internucleotide linkage modifications such as phosphate analogs having achiral and uncharged intersubunit linkages (e.g., Sterchak, E. P. et al., *Organic Chem.*, 52:4202, (1987)), or uncharged morpholino-based polymers having achiral intersubunit linkages (see, e.g., U.S. Pat. No. 5,034,506). Some internucleotide linkage analogs include morpholidate, acetal, and polyamide-linked heterocycles. Other backbone and linkage modifications include, but are not limited to, phosphorothioates, peptide nucleic acids, tricyclo-DNA, decoy oligonucleotide, ribozymes, spiegelmers (containing L nucleic acids, an apatamer with high binding affinity), or CpG oligomers.

Phosphorothioates (or S-oligos) are a variant of normal DNA in which one of the nonbridging oxygens is replaced by a sulfur. The sulfurization of the internucleotide bond dramatically reduces the action of endo- and exonucleases including 5' to 3' and 3' to 5' DNA POL 1 exonuclease, nucleases S1 and P1, RNases, serum nucleases and snake venom phosphodiesterase. In addition, the potential for crossing the lipid bilayer increases. Because of these important improvements, phosphorothioates have found increasing application in cell regulation. Phosphorothioates are made by two principal routes: by the action of a solution of elemental sulfur in carbon disulfide on a hydrogen phosphonate, or by the more recent method of sulfurizing phosphite triesters with either tetraethylthiuram disulfide (TETD) or 3H-1,2-bensodithiol-3-one 1,1-dioxide (BDTD). The latter methods avoid the problem of elemental sulfur's insolubility in most organic solvents and the toxicity of carbon disulfide. The TETD and BDTD methods also yield higher purity phosphorothioates.

Peptide nucleic acids (PNA) are molecules in which the phosphate backbone of oligonucleotides is replaced in its entirety by repeating N-(2-aminoethyl)-glycine units and phosphodiester bonds are replaced by peptide bonds. The various heterocyclic bases are linked to the backbone by methylene carbonyl bonds. PNAs maintain spacing of heterocyclic bases that is similar to oligonucleotides, but are achiral and neutrally charged molecules. Peptide nucleic acids are typically comprised of peptide nucleic acid monomers. The heterocyclic bases can be any of the standard bases (uracil, thymine, cytosine, adenine and guanine) or any of the modified heterocyclic bases described below. A PNA can also have one or more peptide or amino acid variations and modifications. Thus, the backbone constituents of PNAs may be peptide linkages, or alternatively, they may be non-peptide linkages. Examples include acetyl caps, amino spacers such as 8-amino-3,6-dioxaoctanoic acid (referred to herein as 0-linkers), and the like. Methods for the chemical assembly of PNAs are well known.

In some embodiments, the nucleic acid includes one or more chemically-modified heterocyclic bases including, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-β-D-ribofuranosyl)pyridine (2-aminopyridine), and various pyrrolo- and pyrazolopyrimidine derivatives, 4-acetylcytosine, 8-hydroxy-N-6-methyladenosine, aziridinylcytosine, 5-(carboxyhydroxylmethyl) uracil, 5-bromouracil, 5-carboxymethylaminomethyl-2-thiouracil, 5-carboxymethylaminomethyluracil, dihydrouracil, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, N6-methyladenine, 7-methylguanine, 5-methylaminomethyluracil, 5-methoxy-aminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, 2,6-diaminopurine, and 2'-modified analogs such as, but not limited to O-methyl, amino-, and fluoro-modified analogs. Inhibitory RNAs modified with 2'-flouro (2'-F) pyrimidines appear to have favorable properties in vitro.

In some embodiments the nucleic acid includes one or more sugar moiety modifications, including, but are not limited to, 2'-O-aminoethoxy, 2'-O-amonioethyl (2'-OAE), 2'-O-methoxy, 2'-O-methyl, 2-guanidoethyl (2'-OGE), 2'-O,4'-C-methylene (LNA), 2'-O-(methoxyethyl) (2'-OME) and 2'-O—(N-(methyl)acetamido) (2'-OMA).

Methods of gene therapy typically rely on the introduction into the cell of a nucleic acid molecule that alters the genotype of the cell. Introduction of the nucleic acid molecule can correct, replace, or otherwise alters the endogenous gene via genetic recombination. Methods can include introduction of an entire replacement copy of a defective gene, a heterologous gene, or a small nucleic acid molecule such as an oligonucleotide. This approach typically requires delivery systems to introduce the replacement gene into the cell, such as genetically engineered viral vectors.

Methods to construct expression vectors containing genetic sequences and appropriate transcriptional and translational control elements are well known in the art. These methods include in vitro recombinant DNA techniques, synthetic techniques, and in vivo genetic recombination. Expression vectors generally contain regulatory sequences necessary elements for the translation and/or transcription of the inserted coding sequence. For example, the coding sequence is preferably operably linked to a promoter and/or enhancer to help control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters.

Viral vectors include adenovirus, adeno-associated virus, herpes virus, vaccinia virus, polio virus, AIDS virus, neuronal trophic virus, Sindbis and other RNA viruses, including these viruses with the HIV backbone. Also useful are any viral families which share the properties of these viruses which make them suitable for use as vectors. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA.

Gene targeting via target recombination, such as homologous recombination (HR), is another strategy for gene correction. Gene correction at a target locus can be mediated by donor DNA fragments homologous to the target gene (Hu, et al., Mol. Biotech., 29:197-210 (2005); Olsen, et al., J. Gene Med., 7:1534-1544 (2005)). One method of targeted recombination includes the use of triplex-forming oligonucleotides (TFOs) which bind as third strands to homopurine/homopyrimidine sites in duplex DNA in a sequence-specific manner. Triplex forming oigonucleotides can interact with either double-stranded or single-stranded nucleic acids. When triplex molecules interact with a target region, a structure called a triplex is formed, in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a Kd less than 10-6, 10-8, 10-10, or 10-12. Methods for targeted gene therapy using triplex-forming oligonucleotides (TFO's) and peptide nucleic acids (PNAs) are described in U.S. Published Application No. 20070219122 and their use for treating infectious diseases such as HIV are described in U.S. Published Application No. 2008050920. The triplex-forming molecules can also be tail clamp peptide nucleic acids (tcPNAs), such as those described in U.S. Published Application No. 2011/0262406.

Double duplex-forming molecules, such as a pair of pseudocomplementary oligonucleotides, can also induce recombination with a donor oligonucleotide at a chromosomal site. Use of pseudocomplementary oligonucleotides in targeted gene therapy is described in U.S. Published Application No. 2011/0262406.

2. Diagnostic Agents

Exemplary diagnostic materials include paramagnetic molecules, fluorescent compounds, magnetic molecules, and radionuclides. Suitable diagnostic agents include, but are not limited to, x-ray imaging agents and contrast media. Radionuclides also can be used as imaging agents. Examples of other suitable contrast agents include gases or gas emitting compounds, which are radioopaque. Nanoparticles can further include agents useful for determining the location of administered particles. Agents useful for this purpose include fluorescent tags, radionuclides and contrast agents.

III. PHARMACEUTICAL COMPOSITIONS

For those embodiments where the one or more therapeutic, prophylactic, and/or diagnostic agents are encapsulated within a polymeric nanoparticle and/or associated with the surface of the nanoparticle, the percent drug loading is from about 1% to about 80%, from about 1% to about 50%, preferably from about 1% to about 40% by weight, more preferably from about 1% to about 20% by weight, most preferably from about 1% to about 10% by weight. The ranges above are inclusive of all values from 1% to 80%. For those embodiments where the agent is associated with the surface of the particle, the percent loading may be higher since the amount of drug is not limited by the methods of encapsulation. In some embodiments, the agent to be delivered may be encapsulated within a nanoparticle and associated with the surface of the particle.

The formulations described herein contain an effective amount of nanoparticles ("MPPs") in a pharmaceutical carrier appropriate for administration to a mucosal surface, wherein the pharmaceutical carrier is adjusted to be hypotonic. One skilled in the art can routinely adjust tonicity of pharmaceutical carriers, once the desired tissue to be treated is identified, based on the preferred tonicity ranges described herein.

Tonicity is the 'effective osmolality' and is equal to the sum of the concentrations of the solutes which have the capacity to exert an osmotic force across the membrane. A number of different materials can be used to adjust tonicity. For example, the USP 29-NF 24 lists five excipients classified as "tonicity" agents, including dextrose, glycerin; potassium chloride; mannitol; and sodium chloride See, for example, United States Pharmacopeial Convention, Inc. *United States Pharmacopeia 29-National Formulary* 24. Rockville Md.: U.S. Pharmacopeial Convention, Inc.; 2005: 3261; Day, A. Dextrose. In: Rowe R C, Sheskey P J and Owen S C, eds. *Handbook of Pharmaceutical Excipients.* 5th ed. Washington D.C.: American Pharmaceutical Association; 2005: 231-233; Price J C. Glycerin. In: Rowe R C, Sheskey P J and Owen S C, eds. *Handbook of Pharmaceutical Excipients.* 5th ed. Washington D.C.: American Pharmaceutical Association; 2005: 301-303; Price J C. Glycerin. In: Rowe R C, Sheskey P J and Owen S C, eds. *Handbook of Pharmaceutical Excipients.* 5th ed. Washington D.C.: American Pharmaceutical Association; 2005: 301-303; Armstrong N A. Mannitol. In: Rowe R C, Sheskey P J and Owen S C, eds. *Handbook of Pharmaceutical Excipients.* 5th ed. Washington D.C.: American Pharmaceutical Association; 2005: 449-453; Owen S C. Sodium Chloride. In: Rowe R C, Sheskey P J and Owen S C, eds. *Handbook of Pharmaceutical Excipients.* 5th ed. Washington D.C.: American Pharmaceutical Association; 2005: 671-674. Mannitol is an example of a GRAS listed ingredient accepted for use as a food additive in Europe, included in the FDA Inactive Ingredients Database (IP, IM, IV, and SC injections; infusions; buccal, oral and sublingual tablets, powders and capsules; ophthalmic preparations; topical solutions), included in nonparenteral and parenteral medicines licensed in the UK and included in the Canadian Natural Health Products Ingredients Database. A 5.07% w/v aqueous solution is isoosmotic with serum.

Minimally hypotonic formulations, preferably ranging from 20-220 mOsm/kg, provide rapid and uniform delivery of MPP to the entire vaginal surface, with minimal risk of epithelial toxicity. There is a higher osmolality in the colon, such that vehicles with an osmolality above that of blood plasma (generally considered isotonic at ~300 mOsm/kg), leads to improvements in distribution in the colon. The range for improved colon distribution with a hypotonic vehicle in the colon is ~20 mOsm/kg-450 mOsm/kg if a major fraction of the solutes in the formulation consists of $Na^+$ ions, since these will be actively taken up (absorbed) by the epithelium, thus making the formulation effectively hypotonic even though it is hyperosmolal with respect to blood.

A. Pulmonary Formulations

Pharmaceutical formulations and methods for the pulmonary administration of active agents to patients are known in the art.

The respiratory tract is the structure involved in the exchange of gases between the atmosphere and the blood stream. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung, where the exchange of gases occurs.

Formulations can be divided into dry powder formulations and liquid formulations. Both dry powder and liquid formulations can be used to form aerosol formulations. The term aerosol as used herein refers to any preparation of a fine mist of particles, which can be in solution or a suspension, whether or not it is produced using a propellant.

1. Dry Powder Formulations

Dry powder formulations are finely divided solid formulations containing nanoparticle carriers which are suitable for pulmonary administration. Dry powder formulations include, at a minimum, one or more nanoparticle carriers which are suitable for pulmonary administration. Such dry powder formulations can be administered via pulmonary inhalation to a patient without the benefit of any carrier, other than air or a suitable propellant.

In other embodiments, the dry powder formulations contain one or more nanoparticle gene carriers in combination with a pharmaceutically acceptable carrier. In these embodiments, the nanoparticle gene carriers and pharmaceutical carrier can be formed into nano- or microparticles for delivery to the lung.

The pharmaceutical carrier may include a bulking agent or a lipid or surfactant. Natural surfactants such as dipalmitoylphosphatidylcholine (DPPC) are the most preferred. Synthetic and animal derived pulmonary surfactants include Exosurf—a mixture of DPPC with hexadecanol and tyloxapol added as spreading agents, Pumactant (Artificial Lung Expanding Compound or ALEC)—a mixture of DPPC and PG, KL-4-composed of DPPC, palmitoyl-oleoyl phosphatidylglycerol, and palmitic acid, combined with a 21 amino acid synthetic peptide that mimics the structural characteristics of SP-B, Venticute DPPC, PG, palmitic acid and recombinant SP-C, Alveofact—extracted from cow lung lavage fluid, Curosurf—extracted from material derived from minced pig lung, Infasurf-extracted from calf lung lavage fluid, and Survanta—extracted from minced cow lung with additional DPPC, palmitic acid and tripalmitin. Exosurf, Curosurf, Infasurf, and Survanta are the surfactants currently FDA approved for use in the U.S.

The pharmaceutical carrier may also include one or more stabilizing agents or dispersing agents. The pharmaceutical carrier may also include one or more pH adjusters or buffers. Suitable buffers include organic salts prepared from organic acids and bases, such as sodium citrate or sodium ascorbate. The pharmaceutical carrier may also include one or more salts, such as sodium chloride or potassium chloride.

Dry powder formulations are typically prepared by blending one or more nanoparticle carriers with one or more pharmaceutically acceptable carriers. Optionally, additional active agents may be incorporated into the mixture as discussed below. The mixture is then formed into particles suitable for pulmonary administration using techniques known in the art, such as lyophilization, spray drying, agglomeration, spray coating, coacervation, low temperature casting, milling (e.g., air-attrition milling (jet milling), ball milling), high pressure homogenization, and/or supercritical fluid crystallization.

An appropriate method of particle formation can be selected based on the desired particle size, particle size distribution, and particle morphology desired for the formulation. In some cases, the method of particle formation is selected so as to produce a population of particles with the desired particle size, particle size distribution for pulmonary administration. Alternatively, the method of particle formation can produce a population of particles from which a population of particles with the desired particle size, particle size distribution for pulmonary administration is isolated, for example by sieving.

It is known in the art that particle morphology affects the depth of penetration of a particle into the lung. Accordingly, dry powder formulations is processed into particles having the appropriate mass median aerodynamic diameter (MMAD), tap density, and surface roughness to achieve delivery of the one or more active agents to the desired region(s) of the lung. For example, preferred particle morphologies for delivery to the deep lung are known in the art, and are described, for example, in U.S. Pat. No. 7,052,678 to Vanbever, et al.

Particles having a mass median aerodynamic diameter (MMAD) of greater than about 5 microns generally do not reach the lung; instead, they tend to impact the back of the throat and are swallowed. Particles having diameters of about 3 to about 5 microns are small enough to reach the upper- to mid-pulmonary region (conducting airways), but may be too large to reach the alveoli. Smaller particles, (i.e., about 0.5 to about 3 microns), are capable of efficiently reaching the alveolar region. Particles having diameters smaller than about 0.5 microns can also be deposited in the alveolar region by sedimentation.

The precise particle size range effective to achieve delivery to the alveolar region will depend on several factors, including the tap density of particles being delivered. Generally speaking, as tap density decreases, the MMAD of particles capable of efficiently reaching the alveolar region of the lungs increases. Therefore, in cases of particles with low tap densities, particles having diameters of about 3 to about 5 microns, about 5 to about 7 microns, or about 7 to about 9.5 microns can be efficiently delivered to the lungs. The preferred aerodynamic diameter for maximum deposition within the lungs can be calculated. See, for example, U.S. Pat. No. 7,052,678 to Vanbever, et al.

Microparticles cannot diffuse through mucus even if their surface is muco-inert. However, mucus-penetrating particles can be encapsulated in microparticles to impact upper lung, and subsequently release the nanoparticles. In some cases, the particles are spherical or ovoid in shape. The particles can have a smooth or rough surface texture. The particles may also be coated with a polymer or other suitable material to control release of one or more active agents in the lungs.

Dry powder formulations can be administered as dry powder using suitable methods known in the art. Alternatively, the dry powder formulations can be suspended in the liquid formulations described below, and administered to the lung using methods known in the art for the delivery of liquid formulations.

2. Liquid Formulations

Liquid formulations contain one or more nanoparticle carriers suspended in a liquid pharmaceutical carrier. Suitable liquid carriers include, but are not limited to water, saline, and other physiologically acceptable aqueous solutions containing salts and/or buffers, such as phosphate buffered saline (PBS), Ringer's solution, and isotonic sodium chloride, or any other aqueous solution acceptable for administration to an animal or human, which is adjusted to the desired hypotonicity as indicated by the osmotically driven flow of water through the epithelium from the luminal (mucosal) surface to the serosal surface. At certain mucosal surfaces, such as the colon, "hyperosmolal" fluid carriers (defined in the conventional sense, with respect to blood osmolality) may indeed by hypotonic in the colon and induce fluid absorption by the epithelium. Indeed, isotonic formulations have not yet been defined in the lung, and in certain disease states such as Cystic Fibrosis, the osmolality of lung fluid is hyperosmolal (higher than blood osmolality).

Preferably, liquid formulations are mildly hypotonic relative to physiological fluids and of approximately the same pH, ranging e.g., from about pH 4.0 to about pH 7.4, more preferably from about pH 6.0 to pH 7.0. The liquid pharmaceutical carrier can include one or more physiologically compatible buffers, such as a phosphate buffers. One skilled in the art can readily determine a suitable saline content and pH for an aqueous solution for pulmonary administration.

Liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl p-hydroxybenzoate.

In some cases the liquid formulation may contain one or more solvents that are low toxicity organic (i.e. nonaqueous) class 3 residual solvents, such as ethanol, acetone, ethyl acetate, tetrahydofuran, ethyl ether, and propanol. These solvents can be selected based on their ability to readily aerosolize the formulation. Any such solvent included in the liquid formulation should not detrimentally react with the one or more active agents present in the liquid formulation. The solvent should be sufficiently volatile to enable formation of an aerosol of the solution or suspension. Additional solvents or aerosolizing agents, such as a freon, alcohol, glycol, polyglycol, or fatty acid, can also be included in the liquid formulation as desired to increase the volatility and/or alter the aerosolizing behavior of the solution or suspension.

Liquid formulations may also contain minor amounts of polymers, surfactants, or other excipients well known to those of the art. In this context, "minor amounts" means no excipients are present that might adversely affect uptake of the one or more active agents in the lungs.

3. Aerosol Formulations

The dry powder and liquid formulations described above can be used to form aerosol formulations for pulmonary administration. Aerosols for the delivery of therapeutic agents to the respiratory tract are known in the art. The term aerosol as used herein refers to any preparation of a fine mist of solid or liquid particles suspended in a gas. In some cases, the gas may be a propellant; however, this is not required. Aerosols may be produced using a number of standard techniques, including as ultrasonication or high pressure treatment.

In some cases, a device is used to administer the formulations to the lungs. Suitable devices include, but are not limited to, dry powder inhalers, pressurized metered dose inhalers, nebulizers, and electrohydrodynamic aerosol devices. Inhalation can occur through the nose and/or the mouth of the patient. Administration can occur by self-administration of the formulation while inhaling or by administration of the formulation via a respirator to a patient on a respirator.

B. Topical and Ophthalmic Formulations

Topical or enteral formulations can be prepared as aqueous compositions using techniques is known in the art. Typically, such compositions can be prepared as solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, emulsomes, sprays, gels, creams or ointments.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include agents, for example, sugars or sodium chloride, to adjust the tonicity.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristo-amphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for administration upon reconstitution. Suitable buffers include, but are not limited to, phosphate buffers, acetate buffers, and citrate buffers.

Water soluble polymers are often used in pharmaceutical formulations. Suitable water-soluble polymers include, but are not limited to, polyvinylpyrrolidone, dextran, carboxymethylcellulose, and polyethylene glycol.

Sterile solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for ocular administration are preferably in the form of a sterile aqueous solution or suspension of particles formed from one or more polymer-drug conjugates. Acceptable solvents include, for example, water, Ringer's solution, osmolar (PBS), and iso-osmolar sodium chloride solution, which are then adjusted to the desired hypotonicity for the eye as determined using MPP to observe osmotically-induced flow of water (tear fluid). The formulation may also be a sterile solution, suspension, or emulsion in a nontoxic, parenterally acceptable diluent or solvent such as 1,3-butanediol.

In some instances, the formulation is distributed or packaged in a liquid or semi-solid form such as a solution (eye drops), suspension, gel, cream or ointment. Alternatively, formulations for ocular administration can be packed as a solid, obtained, for example by lyophilization of a suitable liquid formulation. The solid can be reconstituted with an appropriate carrier or diluent prior to administration.

Solutions, suspensions, or emulsions for ocular administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers. Solutions, suspensions, or emulsions for ocular administration may also contain one or more tonicity agents to adjust the tonicity of the formulation to be in the moderately hypotonic range. Suitable tonicity agents are well known in the art and some examples include glycerin, mannitol, sorbitol, sodium chloride, and other electrolytes.

Solutions, suspensions, or emulsions for ocular administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for ocular administration may also contain one or more excipients known in the art, such as dispersing agents, wetting agents, and suspending agents.

In still other embodiments, the nanoparticles are formulated for topical administration to mucosa. Suitable dosage forms for topical administration include creams, ointments, salves, sprays, gels, lotions, and emulsions. The compositions may contain one or more chemical penetration enhancers, membrane permeability agents, membrane transport agents, emollients, surfactants, stabilizers, and combination thereof. In some embodiments, the nanoparticles can be administered as a liquid formulation, such as a solution or suspension, a semi-solid formulation, such as a gel, a lotion or an ointment, or a solid formulation. A "gel" is a colloid in which the dispersed phase has combined with the continuous phase to produce a semisolid material, such as jelly.

In some embodiments, the nanoparticles are formulated as liquids, including solutions and suspensions, such as eye drops or as a semi-solid formulation, such as ointment or lotion for topical application to mucosa, such as the eye or vaginally or rectally.

The formulation may contain one or more excipients, such as emollients, surfactants, and emulsifiers.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Foams consist of an emulsion in combination with a gaseous propellant or gas-emitting component.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7.

D. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. Formulations may be prepared using one or more pharmaceutically acceptable excipients, including diluents, preservatives, binders, lubricants, disintegrators, swelling agents, fillers, stabilizers, and combinations thereof.

Excipients, including plasticizers, pigments, colorants, stabilizing agents, and glidants, may also be used to form coated compositions for enteral administration. Delayed release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules.

The nanoparticles may be coated, for example to delay release once the particles have passed through the acidic environment of the stomach. Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions that include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

IV. METHODS OF MAKING MPPs

Techniques for making nanoparticles are known in the art and include, but are not limited to, solvent evaporation, solvent removal, spray drying, phase inversion, low temperature casting, and nanoprecipitation. Suitable methods of particle formulation are briefly described below. Pharmaceutically acceptable excipients, including pH modifying agents, disintegrants, preservatives, and antioxidants, can optionally be incorporated into the particles during particle formation. As described above, one or more additional active agents can also be incorporated into the nanoparticle during particle formation.

V. METHODS OF USING MPP-HYPOTONIC FORMULATIONS

The formulations containing the particles are administered to a mucosal surface in an effective amount of therapeutic to alleviate one or more symptoms, wherein the formulation is hypotonic to enhance uptake of the particles through the mucosa without causing toxicity. This may be using a single-administration sterile packaging containing a solution or suspension such as eye drops or an applicator for a dry powder, gel, ointment, cream or lotion for topical administration to the ocular area, to a region of the mouth (buccal, sublingual), vagina, rectum or aerosol, or it could be formulated for oral administration.

The present invention will be further understood by reference to the following non-limiting examples.

EXAMPLES

Examples 1-6 demonstrate preparation and characterization of mucous penetrating particles ("MPPs"). Examples 7-9 demonstrate the effect of hypotonic formulations on uptake and toxicity of MPPs administered to mucosal tissue.

Materials and Methods

Cholic acid sodium salt, TWEEN® 20, TWEEN® 80, hexadecyltrimethylammonium bromide (CTAB), dioctyl sulfosuccinate sodium (DSS), Polyoxyl 35 hydrogenated castor oil (Cremophor EL) and D-α-tocopherol polyethylene glycol 1000 (Vitamin E-TPGS), were purchased from Sigma (St. Louis, Mo.).

Poly(vinyl alcohol) (Mw=25 kDa with 88% hydrolysis and 6 kDa with 80% hydrolysis), and poly(ethylene-maleic anhydride, 1:1 molar ratio) with Mw~400 kDa were bought from PolySciences (Warrington, Pa.).

Sugar ester D1216 (SE) was a gift from Mitsubishi-Kagaku Foods Co. (Tokyo, Japan).

Alexa Fluor 555 cadaverine was purchased from Invitrogen (Grand Island, N.Y.).

Poly(lactic-co-glycolic acid) (PLGA; LA:GA 50:50) with inherent viscosity of 0.15-0.25 dL/g (MW approximately 15 kDa) was purchased from Lakeshore Biomaterials (Birmingham, Ala.). PLGA(LA:GA 50:50)-PEG copolymers with PEG MW of 10, 5, 2 and 1 kDa, PLA-PEG5k and PCL-PEG5k were custom-synthesized by the Jinan Daigang Biomaterial Co., Ltd, (Jinan, China) and characterized by $^1$H NMR and gel permeation chromatography (GPC). A Shimadzu apparatus equipped with a refractive index detector and two Waters Styragel® HR4 and HR5 columns were used. The analysis was performed at 35° C., using tetrahydrofuran (THF) as the eluent, at a flow rate of 0.5 ml/min. GPC was calibrated with polystyrene standards (Sigma, St. Louis, Mo.).

The chemical composition and molecular weight (MW) of PLGA-PEG block copolymer were characterized by $^1$H NMR. Polymers were dissolved in CDCl$_3$ and $^1$H NMR spectra were recorded using a Bruker 400 REM instrument at 400 MHz. The $^1$H NMR spectra for copolymers in CDCl$_3$ are shown in FIG. 3. Peaks of CH (5.22 ppm) from LA unit, CH$_2$ (4.83 ppm) from GA unit, and CH$_2$CH$_2$ (3.65 ppm) from ethylene oxide unit were integrated, where $I_{5.22}$, $I_{4.83}$, $I_{3.65}$ are the integral intensities of the peaks at 5.22, 4.83 and 3.65 ppm, respectively. Ratio of LA:GA was estimated as $I_{5.22}$:($I_{4.83}$/2).

The MW of PLGA-PEG was estimated as follows:

$$(I_{3.65}/4)/(I_{4.83}/2)=(MW_{PEG}/44)/(MW_{GA}/58)$$

$$(I_{3.65}/4)/(I_{5.22}/1)=(MW_{PEG}/44)/(MW_{LA}/72)$$

$$MW_{PLGA-PEG}=MW_{PEG}+(MW_{GA}+MW_{LA}),$$

where $MW_{PEG}$ is 1, 2, 5 and 10 kDa.

Similarly, the molecular weight of PLA-PEG and PCL-PEG were estimated as follows:

$$(I_{3.65}/4)(I_{5.22}/1)=(MW_{PEG}/44)/(MW_{LA}/72)$$

$$MW_{PLA-PEG}=MW_{PEG}+MW_{LA};$$

$$(I_{3.65}/4)/((I_{4.06}+I_{2.31}/4)=(MW_{PEG}/44)/(MW_{CL}/14)$$

$$MW_{PCL-PEG}=MW_{PEG}+MW_{CL}),$$

where $MW_{PEG}$ is 5 kDa, $I_{4.06}$ and $I_{2.31}$ are the integral intensities of the peaks from PCL at 4.06 and 2.31 ppm, respectively.

Characteristics of various PEG-containing block copolymers are shown in Table 1.

TABLE 1

Characteristics of PEG-containing block copolymers

| Block polymer | PEG [kDa] | LA:GA[a] | PEG content[b] [%] | Mn[c] [kDa] | Mn[d] [kDa] | Mw[d] [kDa] | PDI[d] |
|---|---|---|---|---|---|---|---|
| PLGA-PEG10k | 10 | 54:46 | 21.6[e] | 46.3 | 23.6 | 38.3 | 1.62 |
| PLGA-PEG5k | 5 | 51:49 | 6.0 | 83.0 | 39.2 | 57.8 | 1.48 |
| PLGA-PEG2k | 2 | 52:48 | 6.3 | 31.8 | 19.0 | 27.7 | 1.46 |
| PLGA-PEG1k | 1 | 61:39 | 5.7 | 17.7 | 19.3 | 27.6 | 1.43 |
| PLA-PEG5k | 5 | 100:0 | 5.3 | 94.9 | 64.7 | 87.4 | 1.35 |
| PCL-PEG5k | 5 | — | 6.4 | 77.9 | 54.6 | 73.6 | 1.35 |

[a]The molar ratio of LA:GA was measured by comparing the $^1$H NMR integral intensity at 5.22 ppm (—CH— on lactide), 1.59 ppm (—CH$_3$ on lactide) and 4.83 ppm (—CH$_2$— on glycolide).
[b]PEG content in the block copolymers were determined by $^1$H NMR.
[c]PLGA-PEG molecular weight (Mn) was determined by $^1$H NMR through comparing the integral at 5.22 ppm (—CH— in lactide), 1.59 ppm (—CH$_3$ on lactide), 4.83 ppm (—CH$_2$— in glycolide) and 3.65 ppm (—CH$_2$CH$_2$— in PEG) and by taking into account of the known Mn of PEG. For PCL-PEG, integrals at 4.06 ppm (—O—CH$_2$—) and 2.31 ppm (—CH$_2$—CO—) were analyzed.
[d]Mn, Mw and polydispersity (PDI) were measured by GPC.
[e]PLGA-PEG10 kDa nanoparticles were made from the blending of PLGA15 kDa with PLGA-PEG10 kDa (21.6% PEG content) with overall PEG content in the nanoparticles at 6 wt %.

The total PEG content within nanoparticles was determined by 111 NMR using Broker 400 REM instrument at 400 mHz. The freeze-dried nanoparticles were accurately weighed and dissolved in CDCl3 containing 1 wt % hexadeuterodimethyl sulfoxide (TMS) as internal standard. The PEG content was determined by comparing to a PEG 5 kDa calibration curve achieved from 1H NMR spectra using TMS as internal standard.

The tracking of fluorescently labeled nanoparticles in fresh human cervicovaginal mucus (CVM) was performed. Briefly, 0.6 µl of nanoparticles at suitable dilution was mixed into 20 µl mucus and incubated for 1 hour prior to microscopy. Movies were captured at a temporal resolution of 66.7 ms using a silicon-intensified target camera (VE-1000, Dage-MTI)

mounted on an inverted epifluorescence microscope equipped with 100× oil-immersion objective lens. Trajectories for n>150 particles per experiment were extracted using MetaMorph software (Universal Imaging). Tracking movies (20 s) were analyzed using metamorph software (Universal Imaging, Glendale, Wis.). Time averaged mean square displacement (MSD) and effective diffusivity for each particle were calculated as a function of time scale. Three experiments were performed for each condition. A one tailed, unequal variance Student's t-test was used to evaluate significance (P<0.05).

The ITC experiments were performed at 25° C., using a VP-ITC microcalorimeter (MicroCal Inc., USA). Experiments were performed by injecting 2 mg/ml solution of mucin in DI water into 2 mL sample cell containing nanoparticles with different PEG surface density at a concentration of 1 mg/ml in water with a stirring speed of 481 rpm. A total 28 injections were performed with a spacing of s and a reference power of µcal/s. The first injection of 2 µl mucin solution was followed by 27 injections of 10 µl of mucin solution. Binding isotherms were plotted and analyzed using Origin software, where the ITC measurements were fit to a one-site binding model. Stochoimetry was applied to calculate the binding content of mucin on nanoparticle surface, presented as mg mucin per $m^2$.

Example 1

Preparation of Nanoparticles

Materials and Methods

Biodegradable nanoparticles were prepared by either o/w single emulsion or w/o/w double emulsion method as described in R. C. Mundargi et al, *J Control. Release* 125, 193 (2008), M. Li et al., *Int. J Pharm.* 363, 26 (2008), C. E. Astete and C. M. Sabliov, *J. Biomater. Sci. Polymer Ed.* 17, 247 (2006), and R. A. Jain, *Biomaterials*, 21, 2475 (2000).

Nanoparticles were characterized for size, surface property and drug loading (for drug encapsulated nanoparticles). The displacements of nanoparticles were tracked in fresh, undiluted human CVM using multiple particle tracking.

Nanoparticles Prepared with Different Amounts of PEG

PLGA-PEG nanoparticles were prepared with varying target PEG contents (0, 2, 3, 5, 8, 10 and 25 wt %, referred to as PLGA, PLGA-PEG2%, PLGA-PEG3%, PLGA-PEG5%, PLGA-PEG8%, PLGA-PEG10% and PLGA-PEG25%) using emulsification. The PEG molecular weight 5 kDa was selected since at the same PEG content, 6 wt % PLGA-PEG nanoparticles with PEG ranging from 1 kDa to 10 kDa all can rapidly penetrate mucus. The target PEG contents were controlled by varying the ratio of PLGA and PLGA-PEG during the preparation of nanoparticles. Particle sizes of nanoparticles were controlled to around 100 nm by tuning polymer concentration and emulsification procedure, and all nanoparticles exhibited mono-dispersed diameter with small polydispersity index (less than 0.1) under dynamic light scattering. The nanoparticles were spherically shaped based on TEM study, and PLGA-PEG25% nanoparticles with the highest target PEG content showed less contrast at particle boundaries which probably resulted from the high content of lower electron-density PEG located at the surface.

Results

Table 2 shows the characteristics of the particles prepared as described above.

TABLE 2

Nanoparticle Characteristics

| Target PEG content (wt %) | Diameter [nm] [a] | PDI [a] | ζ-potential [mV] | α [b] | $D_w/D_m$ [c] |
|---|---|---|---|---|---|
| 25 | 91 ± 5 | 0.094 | −2.7 ± 0.7 | 0.89 | 6.0 |
| 10 | 117 ± 7 | 0.097 | −2.4 ± 0.6 | 0.80 | 8.7 |
| 8 | 116 ± 8 | 0.068 | −4.3 ± 0.9 | 0.81 | 7.7 |
| 5 | 106 ± 6 | 0.085 | −7.0 ± 0.7 | 0.78 | 17 |
| 3 | 101 ± 6 | 0.078 | −10 ± 0.1 | 0.53 | 142 |
| 2 | 91 ± 6 | 0.075 | −20 ± 1.4 | 0.31 | 4,000 |
| 0 | 144 ± 6 | 0.056 | −72 ± 2.2 | 0.13 | 38,000 |

[a] Diameter and polydispersity index (PDI) of nanoparticles are measured by the dynamic laser scattering.
[b] The transport rate also can be reflected by the slope α of double logarithmic MSD versus time scale plots (α = 1 represents unobstructed Brownian transport whereas smaller α reflects increased obstruction to particle movement.)
[c] Ratios of the ensemble average diffusion coefficients in mucus ($D_m$) compared to in water ($D_w$) for nanoparticles, and effective diffusivity values were calculated at a time scale of 1 s. Data are means ± SD.

Increasing the target PEG content resulted in a substantial decrease of nanoparticle surface charge (Table 2), and nearly neutral surface charge (approximately 4 mV) was achieved when PEG contents reached 8 wt % and above. Decreased surface charge reflects the increased surface PEG coverage because dense PEG coatings can effectively shield the surface charge of nanoparticles. However, surface charge (zeta-potential) measurement is not able to provide quantitative information for assessing PEG surface density with regard to the number of PEG chains on the surface of a particle. Furthermore, surface charge measurement can be affected by the core materials and the measurement media.

$^1$H NMR was utilized to directly quantify the PEG surface density on nanoparticles. As shown in Table 3, surface PEG content on nanoparticles increases with the increase in the target PEG content. Table 3 shows the PEG surface density of PLGA-PEG nanoparticles with different PEG contents. Surface PEG level was detected by H NMR in $D_2O$ as compared to a standard DSS (1 wt %). The total PEG content in nanoparticles was measured by $^1$H NMR in $CDCl_3$ as compared to a standard TMS (1 wt %). N/A, not applicable.

TABLE 3

Surface PEG Content on Nanoparticles

| Target PEG content (wt %) | Total PEG content in the whole NP (wt %) | PEG content on NP surface (wt %) | PEG surface density [Γ] (chains/100 $nm^2$) [a] | [Γ/Γ*] [b] |
|---|---|---|---|---|
| 25 | 13.0 ± 0.3 | 12.9 ± 1.0 | 29.7 ± 2.9 | 6.7 ± 0.7 |
| 10 | 7.4 ± 0.1 | 7.2 ± 0.2 | 19.4 ± 1.3 | 4.4 ± 0.3 |
| 8 | 6.0 ± 0.3 | 6.0 ± 0.3 | 16.4 ± 1.6 | 3.7 ± 0.4 |
| 5 | 3.7 ± 0.1 | 3.7 ± 0.2 | 10.4 ± 0.2 | 2.4 ± 0.04 |
| 3 | 2.5 ± 0.1 | 2.6 ± 0.1 | 6.5 ± 0.2 | 1.5 ± 0.05 |
| 2 | 1.4 ± 0.4 | 1.4 ± 0.02 | 3.3 ± 0.1 | 0.76 ± 0.02 |
| 0 | N/A | N/A | N/A | N/A |

[a] PEG density [Γ] means the calculated number of PEG molecules per 100 $nm^2$ by assuming that all PEG chains on surface are full length of PEG 5 kDa.
[b] PEG density/full surface coverage [Γ/Γ*]. Full mushroom coverage [Γ*] means the number of unconstrained PEG molecules per 100 $nm^2$. (value <1 indicates mushroom coverage with low PEG density, whereas >1 represents brush regime; when the value >>1 represents a dense brush regime with very high PEG density).
Data (mean ± SD) are the average of at least three different batches of samples.

Example 2

Nanoparticles Prepared with Different Emulsifiers

Materials and Methods

Alexa Fluor 555 cadaverine (AF555) was chemically conjugated to polymers. Nanoparticles were prepared using emulsification. Typically, a mixture (total 50 mg) of PLGA-PEG5k and AF555-labeled PLGA-PEG5k was dissolved in 1 mL dichloromethane (DCM). The oil phase was poured into 5 mL aqueous solution containing 1% emulsifier under sonication (VibraCell, Sonics & Materials Inc., Newtown, Conn.) at 30% amplitude for 2 mins in an ice-water bath to form the oil-in-water emulsion.

The emulsion was poured into another 40 mL aqueous phase of emulsifier solution under magnetic stirring at 700 rpm for at least 3 hours to allow the solvent to evaporate. The solvent was further evaporated by placing the solution in a vacuum chamber for 30 mins. The final nanoparticle suspensions were filtered through 1 μm syringe filter, centrifuged at 20,000 g for 25 mins and thoroughly washed with water.

Emulsifiers including cholic acid sodium salt (CHA), dioctyl sulfosuccinate sodium (DSS), hexadecyltrimethyl ammonium bromide (CTAB), polyvinyl alcohol (PVA), poly(ethylene-maleic anhydride) (PEMA), Saponin, TWEEN20, TWEEN80 and sugar ester D1216 (SE) were tested at a concentration of 1% w/v. CHA solutions at 0.01%-0.5% w/v were also able to make nanoparticles successfully. PLURONIC® F127, F68 solutions and other low MW emulsifiers, like Cremophor EL and Vitamin-E TPGS, were also tested, but unstable emulsions resulted in large aggregated particles.

Table 4 shows the characteristics of nanoparticles prepared using PLGA-PEG (Mn~83 kDa) and PLGA (Mn~15 kDa) and various emulsifiers (1% w/v).

TABLE 4

Characteristics of biodegradable nanoparticles prepared by the emulsification method using PLGA-PEG5k (Mn ~83 kDa) and PLGA (Mn ~15 kDa) and representative emulsifiers (1% w/v).

| Polymer | Emulsifier | Emulsifier MW [Da] | Diameter [nm] | ζ-potential [mV] | $D_w/D_m$ [a] |
|---|---|---|---|---|---|
| PLGA-PEG5k | DSS | 444 | 136 ± 5 | −5.5 ± 0.5 | 3.9 |
| | CHA | 430 | 115 ± 11 | −3.7 ± 0.4 | 5.1 |
| | CTAB | 364 | 77 ± 3 | −4.6 ± 0.7 | 5.6 |
| | Saponin | 1.8k | 108 ± 1 | −7.0 ± 0.7 | 10 |
| | SE | 540 | 97 ± 3 | −4.2 ± 0.3 | 6.8 |
| | TWEEN ® 20 | 1.2k | 156 ± 7 | −3.8 ± 0.3 | 3.5 |
| | TWEEN ® 80 | 1.3k | 152 ± 6 | −4.2 ± 0.3 | 6.8 |
| | F127 | 12.5k | 169 ± 8 | −2.4 ± 0.2 | 4.2 |
| | F68 | 8.4k | 162 ± 5 | −3.3 ± 0.3 | 4.2 |
| | TPGS | 1.5k | 204 ± 7 | −4.8 ± 0.3 | 5.6 |
| | Cremophor | 2.1k | 232 ± 4 | −3.5 ± 0.1 | 3.6 |
| | PVA | 25k | 156 ± 8 | −2.9 ± 0.3 | 40,000 |
| | PEMA | 400k | 185 ± 6 | −42 ± 1.6 | 23,000 |
| PLGA | PVA | 25k | 175 ± 5 | −2.6 ± 1.0 | 19,000 |
| | CHA | 430 | 144 ± 6 | −72 ± 2.2 | 41,000 |

[a] Ratios of the ensemble average diffusion coefficients in water ($D_w$) compared to in mucus ($D_m$) at a time scale of 1 s.

To evaluate the effect of polyethylene glycol molecular weight (PEG MW) on mucus-penetrating property of nanoparticles prepared by the emulsification, CHA was selected as the representative low MW strong emulsifier. PLGA-PEG nanoparticles with different PEG MWs at approximately 6 wt % PEG content were prepared in 0.5% CHA solution. In order to achieve overall 6 wt % PEG content for PLGA-PEG10k nanoparticles, blends of PLGA-PEG10k (21.6 wt %) and PLGA15k were utilized.

Results

Properties of nanoparticles prepared from PEG of various molecular weights (~6 wt % PEG content) are shown in Table 5.

TABLE 5

Characteristics of biodegradable nanoparticles prepared using PEG of various MWs (~6 wt % PEG content) by the emulsifcation method.

| PEG MW [kDa] | Diameter [nm] | ζ-potential [mV] | PEG density [Γ] [a] (#PEG/ 100 nm²) | [Γ/Γ*] [b] | $D_w/D_m$ |
|---|---|---|---|---|---|
| 10 | 124 ± 6 | −2.3 ± 0.1 | 6.7 | 3.0 | 9.6 |
| 5 | 107 ± 3 | −4.2 ± 0.3 | 13.9 | 3.3 | 4.4 |
| 2 | 128 ± 1 | −12 ± 0.9 | 26.2 | 2.5 | 5.0 |
| 1 | 134 ± 5 | −18 ± 1.2 | 45.0 | 2.3 | 7.7 |

[a] PEG density [Γ] indicates the number of PEG molecules per 100 nm². The surface PEG content was quantified by ¹H NMR of nanoparticles in D₂O.
[b] Ratio of PEG density to full surface coverage [Γ/Γ*]. Full surface coverage [Γ*] indicates the theoretical number of unconstrained PEG molecules required to fully coat a 100 nm² surface. ([Γ/Γ*] <1 indicates mushroom regime with low surface PEG density, whereas >1 represents brush regime with high surface PEG density)

Properties of nanoparticles prepared from various concentrations of CHA and PLGA-PEG5k containing 6 wt % PEG are shown in Table 6.

TABLE 6

Characterization of biodegradable nanoparticles using different concentration of emulsifier (CHA) prepared by the emulsification method. PLGA-PEG5k containing 6 wt % PEG was used.

| Emulsifier [w/v %] | Diameter [nm] | ζ-potential [mV] | $D_w/D_m$ |
|---|---|---|---|
| 1 | 115 ± 10 | −3.7 ± 0.4 | 5.1 |
| 0.5 | 107 ± 3 | −4.2 ± 0.3 | 4.4 |
| 0.1 | 142 ± 9 | −3.5 ± 0.6 | 4.1 |
| 0.01 | 125 ± 6 | −5.1 ± 0.5 | 4.3 |

Example 3

Preparation of Drug Encapsulated Nanoparticles

Materials and Methods

Curcumin was selected as a model hydrophobic drug which was dissolved with polymer in DCM. The procedure was similar to that for preparation of unloaded nanoparticles. The prepared curcumin-nanoparticles can be visualized in mucus because of curcumin's intrinsic fluorescence.

BSA was used as a model hydrophilic drug because it is representative of large molecule biologics. BSA-FITC and BSA (10% ratio of BSA-FITC) were dissolved in 0.2 mL 16% w/v aqueous solution at 37° C. This solution was added to 1 mL of 100 mg/ml PLGA-PEG5k in DCM solution during probe sonication (30% amplitude, 1 min with 1 s pulse) in the ice-water bath. The resultant W/O primary emulsion was immediately added to a second water phase (5 mL 1% saponin solution) under sonication (20% amplitude for 2 min). The double emulsion was transferred to another 40 mL 1% saponin solution with magnetic stirring for 3 hours. Nanoparticles were filtered through 1 μm syringe filer, washed and collected by centrifugation. BSA-FITC allowed the possibility to track BSA-loaded nanoparticles in mucus.

Results

The target drug loading for curcumin nanoparticle and BSA nanoparticle was 9.1% and 16.7%, respectively.

Example 4

Estimation of Emulsification Capability

Materials and Methods

PLGA-PEG5k (MW approximately 83 kDa) was used as the model polymer and was dissolved in DCM at 50 mg/ml. A 0.5 ml solution of PLGA-PEG5k in DCM was added to 5 ml aqueous phase containing 1% (w/v) emulsifiers under sonication with 30% amplitude to prepare emulsion using the same method described above. The formed emulsion was added to an additional 20 ml 1% emulsifier solution under magnetic stirring at 700 rpm for 3 hours. The emulsification capability of each emulsifier was estimated by its ability to prevent the formation of aggregated particles. Aggregated particles were collected by centrifugation at 500 g for 20 min, and the remaining nanoparticles in the supernatant were collected by centrifugation at 30,000 g for 25 min. The weight ratio of nanoparticles to aggregated particles was calculated, and used as the index to estimate the emulsification capability of the emulsifier.

Diameter and Surface Charge

Diameter and ξ-potential (surface charge) of nanoparticles were measured using Zetasizer Nano ZS90. Nanoparticles were resuspended in 10 mM NaCl solution. TEM samples were prepared by dropping a dilute suspension of nanoparticle on a TEM grid and allowed to air dry. Particle morphology was characterized using a H7600 transmission electron microscope (Hitachi, Japan).

Encapsulation Efficiency

The encapsulation efficiency of curcumin in nanoparticles was measured by dissolving the freeze-dried nanoparticles in DMSO and measuring the absorbance at 430 nm using Biotek Synergy MX plate reader. The drug content was determined by comparing to the curcumin calibration curve (concentration range 0-50 μg/ml). Absorbance of blank nanoparticle in DMSO at the same polymer concentration was subtracted. The encapsulation efficiency of BSA-FITC was analyzed after alkaline digestion. A known amount of freeze-dried nanoparticles underwent complete hydrolysis in 1M sodium hydroxide. The resultant solution was analyzed using Biotek Synergy MX plate reader at 490 nm excitation wavelength and 525 nm emission wavelength. Standard solutions containing the same amount of polymer and increasing amounts of BSA-FITC at the same processing condition were prepared. The amount of BSA in the nanoparticles was determined by comparison to the BSA-FITC calibration curve.

Drug loading (DL) and encapsulation efficiency (EE) were calculated as follows:

$$DL\ (\%) = \frac{\text{Weight of drug}}{\text{Weight of nanoparticles}} \times 100\%$$

$$EE\ (\%) = \frac{\text{Experimental drug loading}}{\text{Target drug loading}} \times 100\%$$

Results

The results for various emulsifiers are shown in Table 7.

TABLE 7

The encapsulation of model hydrophobic drug (curcumin) and model hydrophilic drug (BSA) in both MPP (CHA and saponin as emulsifier) and CP (PVA as emulsifier) using PLGA-PEG5k (6 wt % PEG)

| Formulation | DL [%] [a] | EE [%] [b] | Diameter [nm] | ζ-potential [mV] | $D_w/D_m$ |
|---|---|---|---|---|---|
| PLGA-PEG5k/CHA (curcumin) | 4.5 | 49 | 156 ± 12 | −5.1 ± 0.5 | 6 |
| PLGA-PEG5k/PVA (curcumin) | 4.3 | 47 | 151 ± 11 | −3.3 ± 1.1 | 2400 |
| PLGA-PEG5k/Saponin (BSA) | 11.4 | 68 | 164 ± 1 | −4.5 ± 0.4 | 36 |
| PLGA-PEG5k/PVA (BSA) | 11.5 | 69 | 218 ± 22 | −2.2 ± 0.8 | 5100 |

[a] Drug loading (DL %) represents the weight content of drug in nanoparticles.
[b] Drug encapsulation efficiency (EE %) represents the ratio of final drug loading in comparison to the theoretical drug loading.

Quantification of Surface Polyethylene Glycol (PEG) Density

The surface PEG density on nanoparticles was determined by 1H NMR using Bruker 400 REM instrument at 400 MHz. Relaxation time was set at 10 s, and ZG at 90°. Nanoparticles with different PEG content were directly prepared in 0.5% CHA D$_2$O solution and suspended in D$_2$O with 1 wt % 3-(trimethylsilyl)-1-propanesulfonic acid, sodium salt as internal standard for $^1$H NMR analysis.

A known weight of PEG 5 kDa (Sigma, St Louis, Mo.) homopolymer in D$_2$O with 1% 3-(trimethylsilyl)-1-propanesulfonic acid, sodium salt was serially diluted to different concentration to set up the calibration curve for the PEG signal in $^1$H NMR, and this calibration curve was used to calculate the surface PEG content on nanoparticles.

A 0.2 ml solution of nanoparticles in D$_2$O was lyophilized and weighed. By assuming all surface PEG chains were full length of PEG 5 kDa, the surface PEG density was calculated as the number of PEG molecules per 100 nm$^2$ surface area on nanoparticles. Control $^1$H NMR experiments were also performed with PLGA nanoparticles prepared by the same method and there were no detectable CHA peaks for PLGA nanoparticles. PEG density, [Γ], is the number of PEG molecules on nanoparticle surface per 100 nm$^2$. It can be calculated by dividing the total PEG content (MPEG, in mole) detected by $^1$H NMR by the total surface area of all nanoparticles as follows:

$$[\Gamma] = \frac{(M_{PEG} \times 6.02 \times 10^{23})}{W_{NP}/d_{NP}/4/3\pi(D/2)^3} \div 4\pi(D/2)^2 \times 100$$

where $W_{NP}$ is the total mass of nanoparticles, $d_{NP}$ is the density of nanoparticle (the density of nanoparticles is assumed to be equal to the density of polymer, 1.21 g/ml for PLGA), and D is the particle diameter as measured by the dynamic light scattering.

Full surface mushroom coverage [Γ*] is the number of unconstrained PEG molecules occupying 100 nm$^2$ of particle surface area. In order to determine [Γ*], the surface area occupied by a single PEG chain was estimated. Using random-walk statistics, a single PEG chain occupies an area at the interface given by a sphere of diameter ξ:

$$\xi = 0.76\ m^{0.5}\ [\text{Å}]$$

where m is the molecular weight of the PEG chain. The surface area occupied by one PEG molecule can be determined from (ξ/2)$^2$. Thus PEG 5 kDa has an unconstrained molecule sphere with diameter of 5.4 nm, and occupies a surface area of 22.7 nm$^2$. Therefore, the number of PEG molecules to fully cover 100 nm$^2$ surface area, [Γ*], is 4.4.

[Γ/Γ*] can be used as an index to measure the PEG density on the nanoparticle surface, where the values <1 indicates low PEG density where PEG molecules are in a mushroom conformation; whereas values >1 indicate high PEG density where PEG molecules are in a brush-like conformation. Similarly, [Γ*] for PEG 10 kDa, 2 kDa and 1 kDa is 2.2, 11 and 22, respectively. The results are shown in Table 2 above.

Table 8 show the PEG surface density of PLGA-PEG nanoparticles with different PEG contents. Surface PEG level was detected by 1H NMR in D20 as compared to a standard DSS (1 wt %). The total PEG content in nanoparticles was measured by 1H NMR in CDCl3 as compared to a standard TMS (1 wt %). N/A, not applicable.

TABLE 8

PEG surface density of PLGA-PEG nanoparticles with different PEG contents

| Target PEG content (wt %) | Total PEG content in the whole NP (wt %) | PEG content on NP surface (wt %) | PEG surface density [Γ] (chains/100 nm$^2$) [a] | [Γ/Γ*] [b] |
|---|---|---|---|---|
| 25 | 13.0 ± 0.3 | 12.9 ± 1.0 | 29.7 ± 2.9 | 6.7 ± 0.7 |
| 10 | 7.4 ± 0.1 | 7.2 ± 0.2 | 19.4 ± 1.3 | 4.4 ± 0.3 |
| 8 | 6.0 ± 0.3 | 6.0 ± 0.3 | 16.4 ± 1.6 | 3.7 ± 0.4 |
| 5 | 3.7 ± 0.1 | 3.7 ± 0.2 | 10.4 ± 0.2 | 2.4 ± 0.04 |
| 3 | 2.5 ± 0.1 | 2.6 ± 0.1 | 6.5 ± 0.2 | 1.5 ± 0.05 |
| 2 | 1.4 ± 0.4 | 1.4 ± 0.02 | 3.3 ± 0.1 | 0.76 ± 0.02 |
| 0 | N/A | N/A | N/A | N/A |

[a] PEG density [Γ] means the calculated number of PEG molecules per 100 nm$^2$ by assuming that all PEG chains on surface are full length of PEG 5 kDa.
[b] PEG density/full surface coverage [Γ/Γ*]. Full mushroom coverage [Γ*] means the number of unconstrained PEG molecules per 100 nm$^2$. (<1 indicates mushroom coverage with low PEG density, whereas >1 represents brush regime; when the value >>1 represents a dense brush regime with very high PEG density).
Data (mean ± SD) are the average of at least three different batches of samples.

The surface PEG density ([Γ], the number of PEG chains per 100 nm$^2$) was calculated and compared with full surface mushroom coverage ([Γ*], the number of unconstrained PEG molecules per 100 nm$^2$). PLGA-PEG3% nanoparticles showed a surface PEG content of 2.6 wt % with density of 6.5 PEG/100 nm$^2$, equal to [Γ]/[Γ*]=1.5, which rendered PLGA-PEG3% with brush conformation of surface PEG coating. High dense brush conformation of PEG coating ([Γ]/[Γ*]>3) was achieved at PEG surface density higher than 10 PEG/100 nm$^2$ (PLGA-PEG5%).

By dissolving the freeze-dried PLGA-PEG nanoparticles in NMR solvent CDCl$_3$, the total PEG content within nanoparticles by $^1$H NMR was measured and it was found that the total PEG contents in nanoparticles (both surface PEG and the PEG embedded within nanoparticle cores) was very close to the surface PEG contents, as shown in Table 5. Almost all the PEG chains in the PLGA-PEG nanoparticles prepared by the emulsification method were detected on the particle surface. The emulsification method involved the evaporation of organic solvent (dichloromethane) from the emulsion droplets and the followed solidification of polymer cores. The slow evaporation of organic solvent provides enough time for hydrophilic PEG chain to diffuse and assemble at the surface of nanoparticles, which resulted in the high partition ratio of PEG to the surface. However, there is significant loss of PEG during the preparation of nanoparticles by the emulsification method, and the PEG loss ratio can be as high as 50% for PLGA-PEG25% nanoparticles.

Similar to previous reports, the loss of PEG may be due to the formation of micelles by the low molecular weight portion of PLGA-PEG in the copolymer, which have higher PEG content and higher hydrophilicity. This part of very small sized particles containing higher PEG content polymers cannot be collected after centrifugation and washing steps, which can be confirmed from the increased average molecular weight of polymer after the formation of nanoparticles in comparison to the raw polymer, measured by gel permeation chromatography. PLGA-PEG10% nanoparticles (117 nm) prepared by nanoprecipitation method (solvent diffusion method) in a control experiment showed 6.5 wt % total PEG content in the nanoparticle and only 89% of PEG chains were detected at surface (equal to 5.8 wt % surface PEG content).

Example 5

Mucus Penetrating Tracking of Nanoparticles

Materials and Methods Human cervical vaginal mucus (CVM) was collected. Briefly, undiluted cervicovaginal secretions from women with normal vaginal flora were obtained using a self-sampling menstrual collection device following a protocol approved by the Institutional Review Board of the Johns Hopkins University. The device was inserted into the vagina for 60 s, removed and placed into a 50 ml centrifuge tube and centrifuged at 1000 rpm for 2 min to collect the secretions.

The tracking of fluorescently labeled nanoparticles in fresh human cervicovaginal mucus (CVM) was performed. Briefly, 0.6 µl of nanoparticles at suitable dilution was added to 20 µl mucus within a custom-made chamber slide and incubated at room temperature for 1 hour prior to microscopy. The trajectories of nanoparticles in CVM were recorded by using multiple particle tracking (MPT). 20 s movies were captured at a temporal resolution of 66.7 ms using a silicon-intensified target camera (VE-1000, Dage-MTI) mounted on an inverted epifluorescence microscope equipped with 100× oil-immersion objective (N.A., 1.3). Tracking movies (20 s) were analyzed using MetaMorph software (Universal Imaging, Glendale, Wis.).

Time averaged mean square displacement (MSD) and effective diffusivity for each particle were calculated as a function of time scale:

$$<\Delta r2(\tau)> = [x(t+\tau)-x(t)]^2 + [y(t+\tau)-y(t)]^2$$

where x and y represent the nanoparticle coordinates as a function of time and τ is the time lag.

Curcumin-loaded nanoparticles and FITC-BSA-loaded nanoparticles were tracked in human CVM in the same manner using the fluorescence from either encapsulated curcumin or BSA-FITC. Particle penetration into a mucus layer was modeled using Fick's second law and diffusion coefficients obtained from tracking experiments.

Results

Figure 1B:
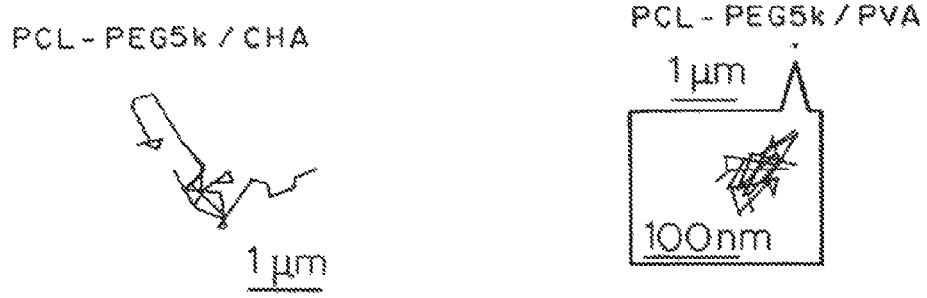
Figure 1C:
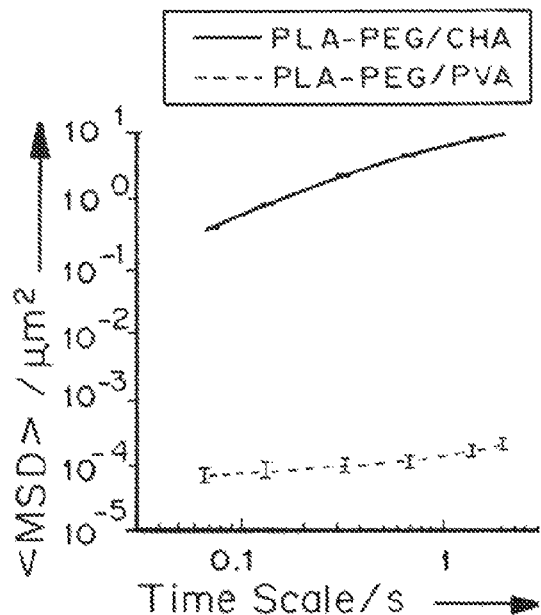
FIGS. 1c and 1d are graphs showing the ensemble-averaged geometric mean square displacements (<MSD>/$\mu m^2$) as function of time (time scale/s).
Figure 1D:
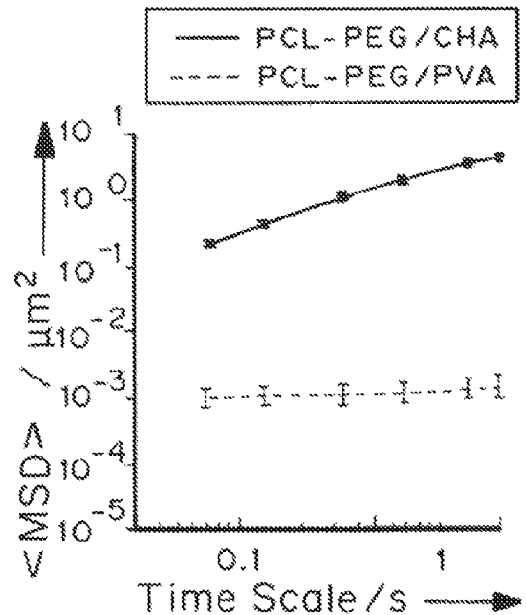
Figure 1E:
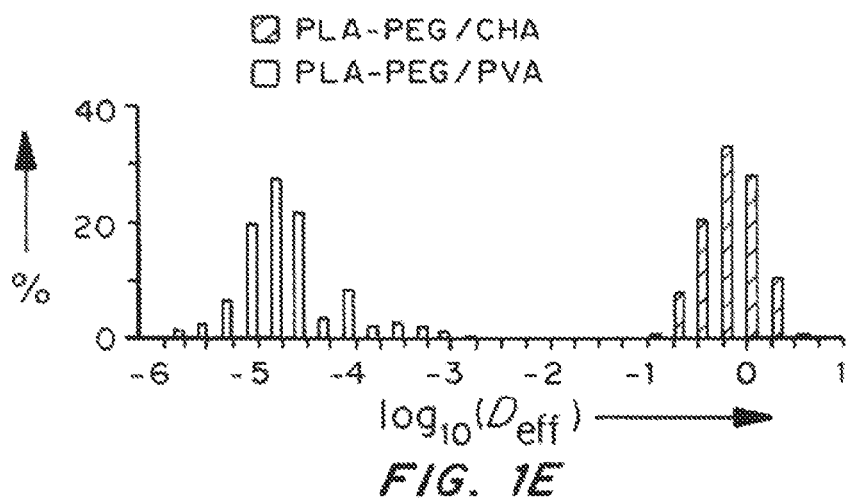
FIGS. 1e and 1f are graphs showing the penetrable fraction as a function of distributions of the logarithms of individual particle effective diffusivities ($D_{eff}$) at a time scale of 1 s.
Figure 1F:
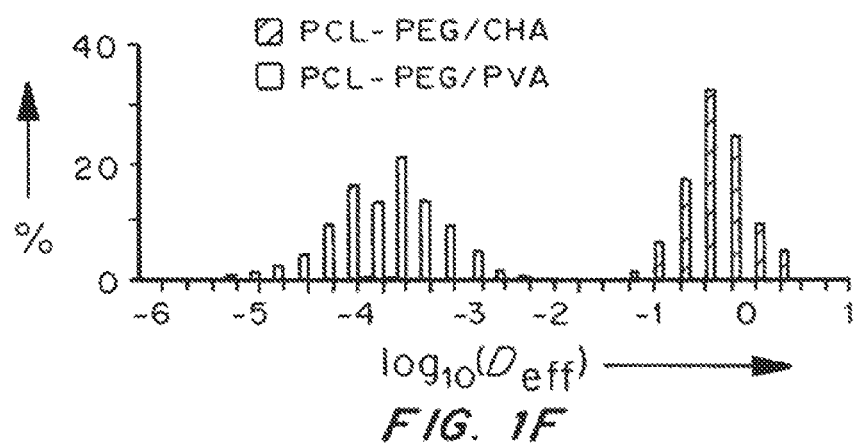
Figure 1G:
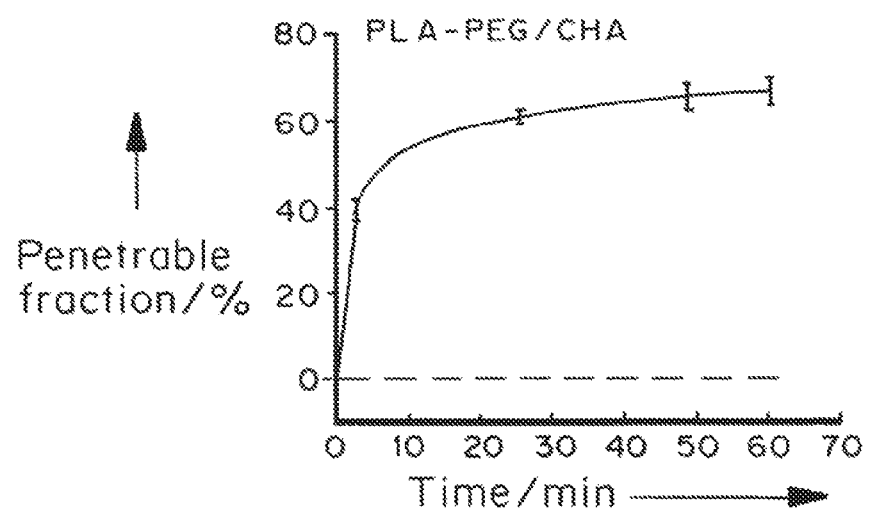
FIGS. 1g and 1h are graphs showing the estimated fraction of particles capable of penetrating a physiological 30 μm thick mucus layer over time. Data represent three independent experiments with ≥120 nanoparticles tracked for each experiment. Error bars are presented as s.e.m.
Figure 1H:
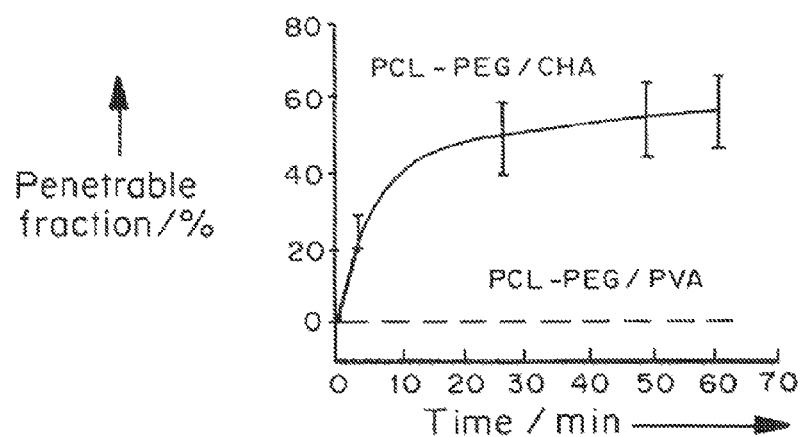

The comparison of transport of human CVM of PLA-PEG and PCL-PEG nanoparticles containing CHA and PVA prepared by emulsification is shown in FIGS. 1a-h. FIGS. 1a and 1b show representative trajectories of PLA-PEG and PCL-PEG nanoparticles containing CHA and PVA. FIGS. 1c and 1d are graphs showing ensemble-averaged geometric mean square displacements (<MSD>) as function of time scale. FIGS. 1e and 1f are graphs showing the distributions of the logarithms of individual particle effective diffusivities (Deff) at a time scale of 1 s. FIGS. 1g and 1h are graphs showing the estimated fraction of particles capable of penetrating a physiological 30 µm thick mucus layer over time. Data represent three independent experiments with ≥120 nanoparticles tracked for each experiment. Error bars are presented as s.e.m. This data shows immobilization of nanoparticles made using PVA and rapid mucus penetration for nanoparticles made using a low MW emulsifier, CHA, with effective diffusivities similar to those measured for PLGA-PEG5k nanoparticles.

Figure 2A:
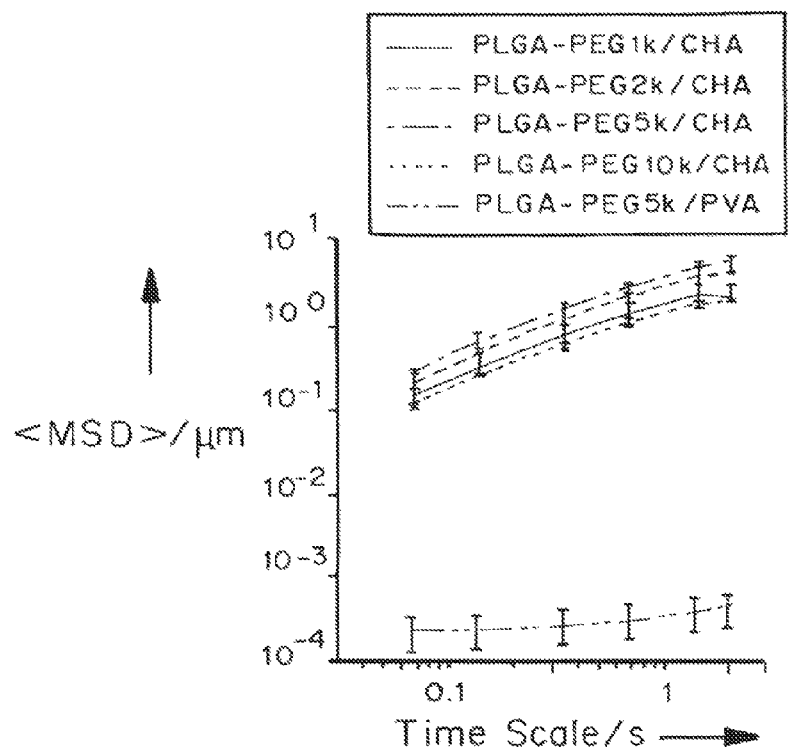
FIGS. 2a and 2b show the effect of PEG MW on transport rate of MPP in human cervicovaginal mucus.
Figure 2B:
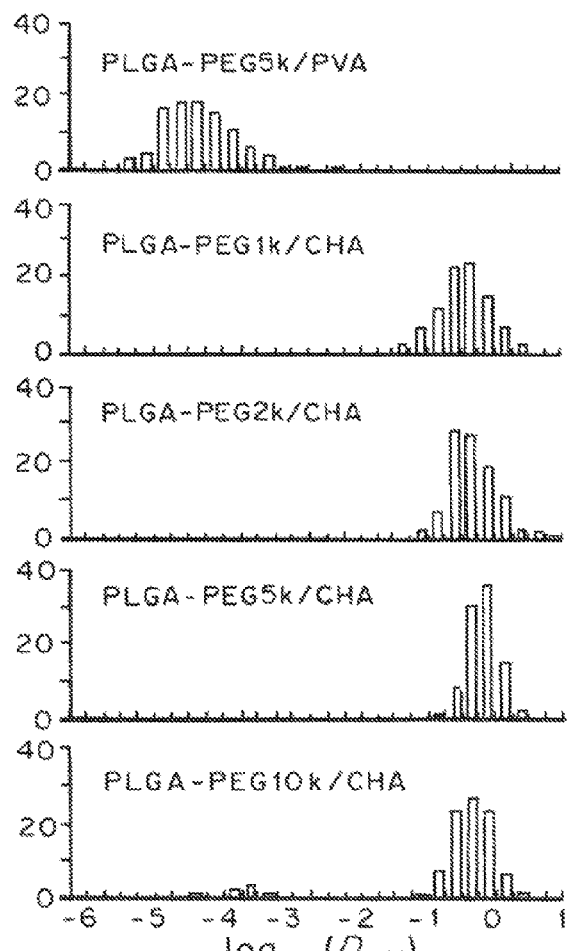

The effect of PEG molecular weight on transport rate of MPPs in CVM is shown in FIGS. 2a and 2b. FIGS. 2a and 2b show the effect of PEG MW on transport rate of MPP in human cervicovaginal mucus. FIG. 2a is a graph showing the ensemble-averaged geometric mean square displacement <MSD> as a function of time scale. FIG. 2b is a graph showing the distributions of the logarithms of individual particle effective diffusivities (Deft) at a time scale of 1 s. Particles were prepared with the emulsification method using PLGA-PEG (6 wt % PEG). Data represent three independent experiments with ≥120 nanoparticles tracked for each experiment. Error bars are presented as s.e.m. These particles all rapidly penetrated mucus (see also Table 5).

The nanoparticle surface charge was inversely proportional to the PEG MW and varied from −18 mV (1 kDa) to −2.3 mV (10 kDa). The surface PEG density [Γ] (number of PEG per 100 nm2) measured by 1H NMR decreased as PEG MW increased. However, the ratio [Γ/Γ*][11] of surface PEG density to the theoretical PEG density required for the formation of a brush-like PEG coating [Γ*] was greater than 2 (Table 5), regardless of PEG MW, indicating the presence of a dense brush-like coating of PEG on the surface of PLGA-PEG(1-10 kDa)/CHA nanoparticles.

Figure 3A:
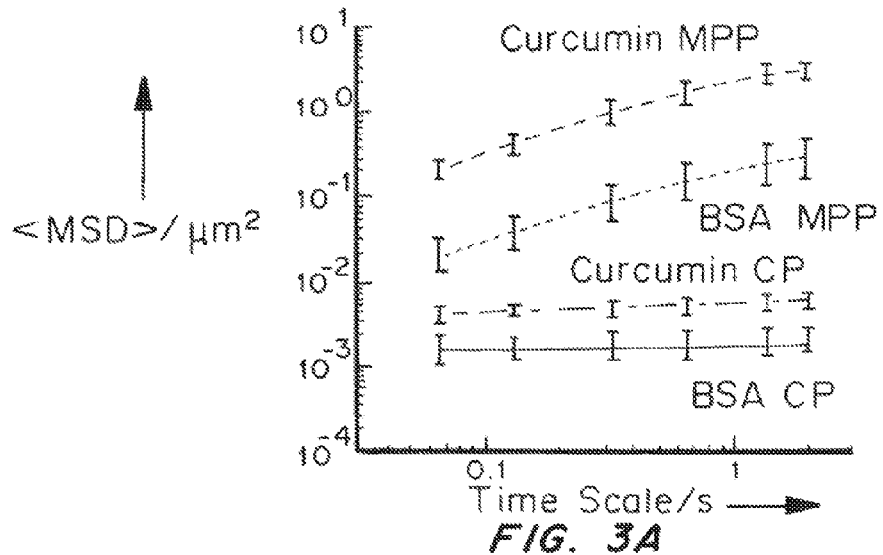
FIG. 3a is a graph showing the ensemble-averaged geometric mean square displacement <MSD/$\mu m^2$> as a function of time scale.
Figure 3B:
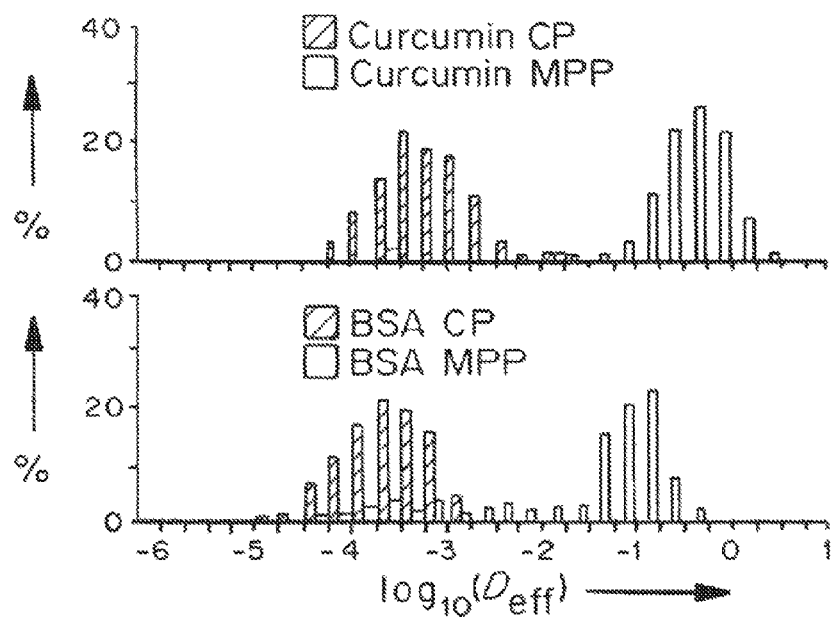
FIG. 3b is a graph showing the distributions of the logarithms of individual particle effective diffusivities ($D_{eff}$) at a time scale of 1 s.
Figure 3C:
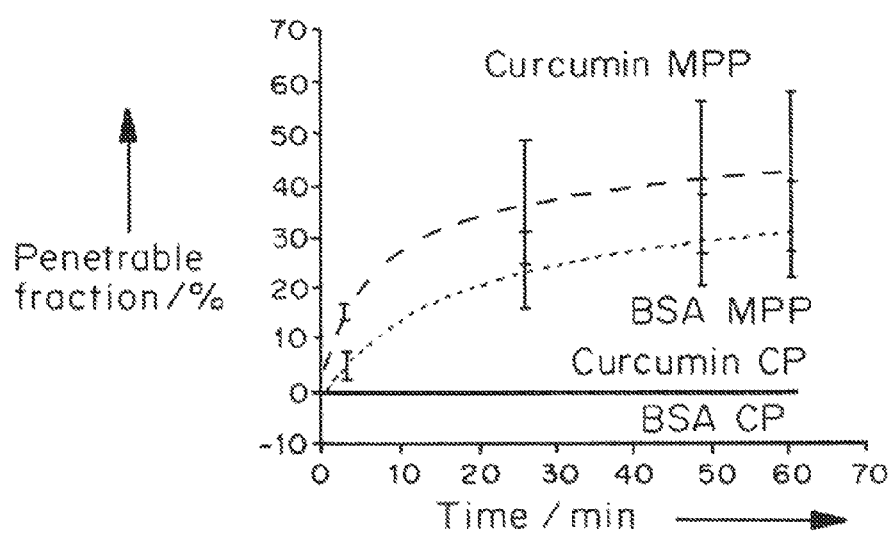
FIG. 3c is a graph showing the estimated fraction of particles predicted to be capable of penetrating a 30 μm thick mucus layer over time. Data represent three independent experiments with ≥120 nanoparticles tracked for each experiment. Error bars are presented as s.e.m.

FIGS. 3a-3c shows the transport rates of curcumin and BSA loaded MPPs and conventional particles (CPs). FIG. 3a is a graph showing the ensemble-averaged geometric mean square displacement <MSD> as a function of time scale. FIG. 3b is a graph showing the distributions of the logarithms of individual particle effective diffusivities (Deft) at a time scale of 1 s. FIG. 3c is a graph showing the estimated fraction of particles predicted to be capable of penetrating a 30 μm thick mucus layer over time. Data represent three independent experiments with ≥120 nanoparticles tracked for each experiment. Error bars are presented as s.e.m. Curcumin and BSA-loaded nanoparticles rapidly diffused in mucus at rates only 6 and 36-fold slower than in water at τ=1 s, respectively (FIG. 3a). In contrast, nanoparticles prepared with PVA were immobilized in CVM (FIG. 3b), with transport rates more than 2,000-fold slower than in water.

PLGA nanoparticles without PEG coating were completely immobilized within mucus with diffusivities 38,000 times slower than the diffusivities of same sized nanoparticles in water. The presence of PEG surface coating on nanoparticles significantly improved their diffusion through the highly viscoelastic mucus, PLGA-PEG3% with surface PEG density of 6.5 PEG/100 nm² showed increased Dw/Dm value up to 142. Further increasing the surface PEG density up to 10.4 PEG/100 nm², PLGA-PEG5% nanoparticles were only 17-fold slower than their diffusion in water. More than 90% of the nanoparticles were diffusive when surface PEG density was higher than 16.4 PEG/100 nm² (PLGA-PEG8%). Further increase of the surface PEG density likely will not significantly improve the particle diffusivity within mucus, since a surface density of 16.4 PEG/100 nm² is already capable to efficiently shield the binding of mucus components. Approximately 50-70% nanoparticles of PLGA-PEG8%, 10% and 25% were able to penetrate physiological 30 μm thick mucus layer within 60 mins, are much higher rates than PLGA-PEG5%, PLGA-PEG3% (dense coating), PLGA-PEG2% (low coating) and PLGA (no coating).

Example 6

Stability of Nanoparticles in Mucus

Materials and Methods
The stability of nanoparticles in mucus by minimizing the adhesive interaction between particles and mucus components is an important criterion for their application as mucus-penetration drug carriers in vivo. The change in nanoparticle size in the presence of mucin as the indication of mucin binding was studied to determine the stability of nanoparticles with different PEG surface density at the presence of mucin. Mucin extracted from bovine submaxillary gland was chosen as a model mucin because mucin is the main component of mucus and mucin from bovine submaxillary gland shares similarity with human CVM in both structure and physiological properties.

Nanoparticles were incubated with mucin solution (10 mg/ml) and the change of particle size over time was monitored.

Results
PLGA-PEG nanoparticles with PEG surface density ≥16.4 PEG/100 nm² were stable in mucin solution retaining their hydrodynamic diameter during the whole 3 hour incubation, and at these PEG surface densities the PEG coatings were in high dense brush conformation ([Γ]/[Γ*]>3). In contrast, PLGA-PEG5% nanoparticles with surface density of 6.5 PEG/100 nm² showed approximately 5% increase in particle diameter after the incubation with mucin solution even only for 5 mins, and the PEG surface density on these PLGA-PEG5% nanoparticles already resulted in a brush PEG coating ([Γ]/[Γ*]>1). Therefore, brush PEG coatings alone are not enough to completely shield the mucin binding. There was a progressive increase in particle size with decreased PEG surface density from brush conformation to mushroom conformation. Without PEG coating, PLGA nanoparticles exhibited a dramatic size increase from 109±2 nm to 207±9 nm within 5 min of incubation in mucin.

Figure 4A:
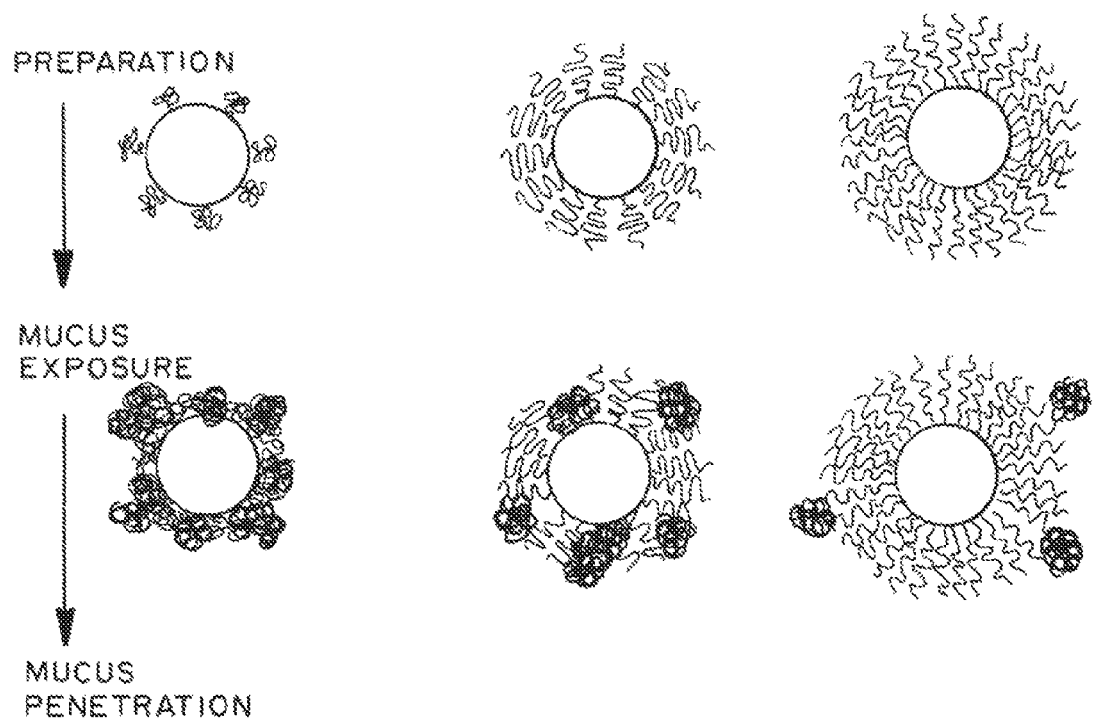
FIGS. 4a-c are schematics illustrating the influence of surface PEG coverage ([Γ/Γ*]) on mucus penetration of nanoparticles.
Figure 4A:
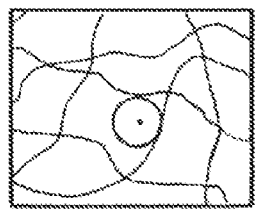
Figure 4B:
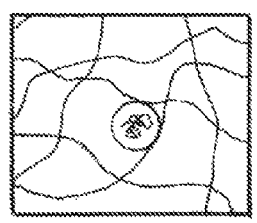
Figure 4C:
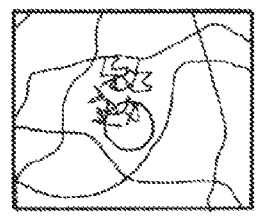

FIG. 4a is a schematic illustrating the influence of surface PEG coverage ([Γ/Γ*]) on mucus penetration of nanoparticles. The upper panels show the preparation of PLGA-PEG nanoparticles with surface PEG coating at increasing coverage. As surface PEG coverage increases, PEG regime changes from mushroom (neighboring PEG chains do not overlap, [Γ/Γ*]<1, FIG. 4a), to brush (neighboring PEG chains overlap, 1<[Γ/Γ*]<3, FIG. 4b), to dense brush ([Γ/Γ*] >3, FIG. 4c). The middle panels illustrate how PEG coverage determines the muco-adhesive interaction after mucus exposure. At low PEG coverage ([Γ/Γ*]<1), mucin fibers strongly adhere to nanoparticle core. At middle PEG coverage (1<[Γ/Γ*]<3), mucin fibers still can partially absorb to the nanoparticle core. At high ([Γ/Γ*]>3) PEG coverage, the nanoparticle cores were completely shielded by the bioinert PEG corona resulting in no absorption of mucin to nanoparticles. The lower panels show that nanoparticles with low PEG coverage are immobilized in mucus, nanoparticles with middle PEG coverage are hindered or even immobilized in mucus, nanoparticles with high and very high PEG coverage are able to rapidly penetrate mucus.

Example 7

Effect of Osmolarity of Particle Solution on Distribution and Retention of Nanoparticle in Vaginal and Colon Mucosal Tissue Mucus penetrating nanoparticles (MPP) that avoid being adhesively trapped by the mucus layers present on mucosal surfaces were used to study this effect at mucosal surfaces. Extremely dense coatings of low molecular weight (5 kDa) polyethylene glycol (PEG) were covalently attached to the surface of fluorescent 100 nm carboxyl-modified polystyrene (PS) particles to produce mucuspenetrating PS-PEG nanoparticles. Uncoated nanoparticles ("conventional particles", or "CP") stick to mucins. CP do not penetrate the mucus layers well and, instead, aggregate in the lumen of flash-frozen whole mouse colonic and vaginal tissue. However, MPP penetrated the mucus barrier all the way to the underlying epithelium, producing a continuous "layer" of particles in both mouse rectal and vaginal tissue. The great absorptive capacity of mucosal surfaces could rapidly "suck" the MPPs, but not CPs, through the mucus layers if the particles are administered in a hypoosmolar solvent, like pure water. Particle administration in a hypoosmolar solution, such as ultrapure (UP) water, causes fluid absorption by the tissue underlying the mucus layers in order to reach osmotic equilibrium, thus drawing in MPP by convection.

There have been recent reports detailing the negative side effects of administering highly hyperosmolar formulations used for vaginal and rectal delivery, which can cause significant toxicity and epithelial erosion (Fuchs et al. *J Infect Dis* 195, 703-710 (2007); Lacey et al. *Int J STD AIDS* 21, 714-717 (2007)). However, mildly hypoosmolar fluids have not been shown to have the same toxicity profile.

Materials and Methods

The distribution of fluorescent 100 nm mucus-penetrating PEGylated polystyrene particles on cross-sections of flash-frozen whole colon tissue administered in either (A) 1×PBS or (B) ultrapure water was examined. Tissue was excised immediately after administration and was stained with DAN to show cell nuclei.

Distribution of fluorescent 100 nm mucus-penetrating PEGylated polystyrene particles on cross-sections of flash-frozen whole vaginal tissue administered in either (A) 1×PBS or (B) ultrapure water was also examined. Tissue was excised immediately after administration and was stained with DAPI to show cell nuclei.

Fluorescence of whole mouse vaginal tracts and colorectal tissue after initial administration of fluorescent nanoparticles in either UP water (hypoosmolar) or PBS (isoosmolar) was then assessed.

To evaluate nanoparticle retention, 5 µL of red fluorescent CPs or MPPs were administered intravaginally. Whole cervicovaginal tracts were obtained at 0, 2, 4, and 6 h and placed in a standard tissue culture dish. For each condition and time point, n>7 mice were used. Fluorescence images of the tissues were obtained using the Xenogen IVIS Spectrum imaging device (Caliper Life Sciences). Quantification of fluorescent counts per unit area was calculated using the Xenogen Living Image 2.5 software.

Results

MPP quickly begin to line the vaginal and colorectal epithelium when administered in hypoosmolar solution.

The percentage of MPP (PSPEG) and CP (PS) retained in the mouse vaginal tract over time after administration in UP water was measured. After 6 h, 57% of MPP and 7% of CP remain in the CV tract.

MPP were retained in the vaginas of mice at much higher amounts for at least 6 hours.

Biodegradable MPP containing FITC intravaginally was administered in UP water. As a comparison, FITC in the standard isoosmolar placebo gel, hydroxyethlycellulose (HEC), was administered. After 24 h, the vaginal tissue was excised and flattened between two glass slides. The hypotonically delivered MPP appeared to fully coat the epithelium, whereas the FITC was sparsely distributed. MPP dramatically improved the epithelial distribution of an otherwise poorly distributed entity.

Example 8

Distribution of MPPs in Vaginal Tissues as a Function of Osmolarity

The studies in Example 7 demonstrated that MPP that do not adhere to mucus are capable of rapidly diffusing through human and mouse cervicovaginal mucus (CVM), leading to penetration deep into the more slowly cleared mucus layers in the rugae, coating the entire vaginal surface and residing in the vagina longer than conventional mucoadhesive nanoparticles (CP), published by Ensign, et al *Sci Transl Med* 4, 138ra179 (2012).

One key to the improved vaginal distribution and retention by MPP was administering the nanoparticles in a hypotonic solution. When delivered in a hypotonic solution, MPP rapidly accumulated on the entire vaginal surface, arriving there much more rapidly than expected based on diffusion alone. When fluid is pressure-induced to flow through the mucus gel, MPP flow through the mucus along with the flowing fluid (i.e., by solvent drag). Studies were conducted to determine if a similar effect would occur if drugs and MPP were delivered into the vagina in hypotonic formulations. This study investigated hypotonic vaginal delivery of free drug as well as by MPP to determine whether hypotonic delivery might provide improved distribution, retention, and protection.

Materials and Methods

Animal Model

Female 6-8 week-old CF-1 mice were purchased from Harlan (Indianapolis, Ind.). Mice were housed in a reverse light cycle facility (12 h light/12 h dark), to enable selection of mice in a naturally cycling estrus state. The mouse vagina during the estrus phase of the estrous cycle is most similar to the human vagina. Barrier properties to nanoparticles in estrus phase mouse mucus closely mimic the barrier properties to nanoparticles in human CVM. Thus, mice in estrus phase, as determined visually by the appearance of the vaginal introitus, were used for all distribution and retention studies. Mice used for vaginal HSV-2 protection and susceptibility studies were given a subcutaneous flank injection of 2.5 mg Depo-Provera (Pharmacia & Upjohn Company, New York, N.Y.) in 100 phosphate-buffered saline (PBS) 7 days prior to experiments. This treatment is commonly used to increase susceptibility to vaginal HSV-2 infection. All experimental protocols were approved by the Johns Hopkins Animal Care and Use Committee.

Nanoparticle Preparation and Characterization

Fluorescent, carboxyl(COOH)-modified polystyrene (PS) nanoparticles 100 nm in diameter were purchased from Molecular Probes (Eugene, Oreg.). To produce MPP, PS particles were covalently modified with 5 kDa amine-modified PEG (Creative PEGworks, Winston Salem, N.C.) as previously described by Nance et al *Sci Transl Med* 4, 149ra119 (2012). Particle size and ζ-potential were determined by dynamic light scattering and laser Doppler anemometry, respectively, using a Zetasizer Nano ZS90 (Malvern Instruments, Southborough, Mass.). Size measurements were performed at 25° C. at a scattering angle of 90°. Samples were diluted in 10 mM NaCl solution (pH 7) and measurements performed according to instrument instructions. A near neutral ζ-potential was used to confirm PEG conjugation, and particles were tested for mucus-penetrating ability in human CVM as previously described by Lai et al, *Proc Natl Acad Sci USA* 104, 1482-1487 (2007) and Wang et al. *Angew Chem Int Ed Engl* 47, 9726-9729 (2008). These particles were previously shown to rapidly penetrate estrus phase mouse vaginal mucus. The osmolality of solutions was measured using a Wescor Vapro vapor pressure osmometer.

Drug and Nanoparticle Distribution in the Vagina

Doxorubicin (NetQem, Durham, N.C.) was dissolved at 1 mg/ml concentration in either PBS (isoosmolar with respect to blood) or ultrapure water (hypoosmolar). For 1 liter of 1×PBS, 800 ml of distilled water; 8 g of NaCl; 0.2 g of KCl;

1.44 g of $Na_2HPO_4$; 0.24 g of $KH_2PO_4$; adjust the pH to 7.4 with HCl, add distilled water to a total volume of 1 liter.

Doxorubicin was vaginally administered both isoosmotically and hypoosmotically to mice in two different conditions. The "non-ambulatory" group was anesthetized with an intraperitoneal injection of Avertin working solution (prepared according to Johns Hopkins ACUC guidelines) and remained supine for 1 hr prior to tissue collection. The "ambulatory" group was anesthetized with fast-acting, inhalable isoflurane, such that the mice immediately awoke and were ambulatory for 10 min prior to tissue collection. The vaginal tissues were then collected, sliced open longitudinally, flattened, and clamped between two glass slides sealed shut with super glue. This procedure completely flattens the tissue, exposing the surfaces that were infolded from the lumen. Tissues were imaged on a epifluorescence microscope (Nikon E6100) at 2× magnification. Doxorubicin is fluorescent (ex/em 470/590). Untreated control tissues were imaged to ensure that the fluorescent signal from Doxorubicin was well above the tissue autofluorescence. The low magnification captured large portions of the tissue, so only 2-3 images were needed to observe the entire tissue surface. The images were 'thresholded' to draw region of interest boundaries around the fluorescent signal, and then the area covered quantified using ImageJ software. An average percentage coverage was determined for each mouse, and these values were averaged over groups of n=5 mice.

To capture the distribution of MPP due to immediate fluid absorption dynamics, 20 µl of either isoosmolar (PBS) or hypoosmolar (ultrapure water) MPP solution was administered vaginally. The higher volume of solution helped ensure that the lumen would be filled with fluid, and the particles were diluted (0.01% w/v) such that concentration gradients would be visually evident. The mice were anesthetized with isoflurane, and sacrificed immediately after particle administration. The vaginal tissue was quickly excised and flash-frozen in Tissue-Tek O.C.T. Compound. Transverse sections were obtained at various points along the length of the tissue using a Leica CM-3050-S cryostat. The thickness of the sections was set to 6 µm to achieve single cell layer thickness. The sections were then stained with ProLong Gold antifade reagent with DAPI to visualize cell nuclei and retain particle fluorescence. Fluorescent images of the sections were obtained with an inverted epifluorescence microscope (Zeiss Axio Observer). For MPP distribution with varying solution osmolality, particle solutions (0.08% w/v) were prepared from varying ratios of PBS and ultrapure water. Mice were anesthetized with isoflurane, and 5 µl of particle solution was administered vaginally. After 10 min, tissues were collected, flash-frozen, sectioned, and stained following the procedures outlined for observing fluid absorption dynamics. In order to quantify MPP vaginal tissue coverage, mice were anesthetized with isoflurane, and 5 µl of nanoparticle solution was administered vaginally. Within 10 min, tissues were excised, sliced open longitudinally, and then flattened as described for drug distribution experiments. Control tissues were imaged to ensure that the fluorescent signal was well above the tissue autofluorescence. Tissues were imaged at 10× magnification using an inverted epifluorescence microscope (Zeiss Axio Observer), and 8 images per tissue were acquired. The coverage was quantified as previously outlined for drug distribution experiments.

Drug and Nanoparticle Retention in the Vagina

Doxorubicin was dissolved at a concentration of 1 mg/ml in phosphate buffered saline ("PBS") (isoosmolar with respect to blood) or ultrapure water (hypoosmolar). Mice were anesthetized with an intraperitoneal injection of Avertin prior to intravaginal administration of 5 µl of Doxorubicin solution. The mice remained supine for 10 min to ensure that solution "drip out" would not affect the retention measurement. Then, the whole cervicovaginal tracts were excised and placed in a standard tissue culture dish. Fluorescence images of the tissues were obtained using the Xenogen IVIS Spectrum imaging device (Caliper Life Sciences). To account for potential differences in Doxorubicin solution fluorescence, vials of both isoosmolar and hypoosmolar Doxorubicin solutions were included in the image. The ratio of the intensity of the two solutions was used to normalize the tissue fluorescence for each group. Quantification of fluorescent counts per unit area was calculated using the Xenogen Living Image 2.5 software. The average for the isoosmolar and hypoosmolar groups was normalized to the isoosmolar group.

Red fluorescent MPP were suspended in either PBS (isoosmolar) or ultrapure water (hypoosmolar) at 0.2% (w/v). Mice were either anesthetized with an intraperitoneal injection of Avertin ("non-ambulatory") or by inhalation of isoflurane ("ambulatory") as described previously for drug distribution experiments. Five µl of either isoosmolar or hypoosmolar MPP solution was administered intravaginally. After 1 h for non-ambulatory mice, or 10 min for ambulatory mice, whole cervicovaginal tracts were excised and placed in a standard tissue culture dish. Fluorescence images were taken and quantified as described for drug retention. As a reference point for MPP retention, 5 µl of MPP solution was carefully pipetted into the vagina after the whole cervicovaginal tract was already removed and placed in a tissue culture dish. This approach was used for MPP (but not Doxorubicin), because the nanoparticles do not penetrate the tissue; therefore there is no potential effect from differential tissue penetration on the fluorescent signal. The retention was then calculated as a percentage of the average reference tissue signal.

HSV-2 Infection Mouse Model

Mice received 20 µl of 10 mg/ml acyclovir monophosphate dissolved in either PBS (isoosmolar) or ultrapure water (hypoosmolar) immediately before use. This drug was shown to give partial protection in a mouse model of vaginal HSV-2 infection. Mice were dosed either 1 min or 60 min prior to viral inoculum. Mice were then challenged with 10 µl of inoculum containing HSV-2 strain G (ATCC #VR-724, 2.8× $10^7$ $TCID_{50}$ per ml). For protection studies, HSV-2 was diluted 10-fold with Bartel's medium to deliver 10 $ID_{50}$, a dose that typically infects 85-90% of control mice. For osmotic-induced susceptibility tests, virus was diluted 10-fold with Bartel's medium and further diluted 10-fold in either Bartel's medium (isoosmolar) or deionized water (hypoosmolar) to the $ID_{50}$, a dose that infects half of the mice. Mice were assessed for infection three days later after inoculation by culturing a PBS vaginal lavage on human foreskin fibroblasts (Diagnostic Hybrids, MRHF Lot #440318W). In this model, input (challenge) virus is no longer detectable in lavage fluid if it is collected more than 12 h after the challenge.

Statistics

The Wilcoxon rank-sum test was used to compare data sets. This test is non-parametric, and more appropriate in situations where a Gaussian distribution cannot be assumed. For HSV-2 infection studies, statistical significance was determined using Fisher's exact test, two-tailed distribution.

Results

Effect of Tonicity on Vaginal Drug Distribution

Figure 5A:
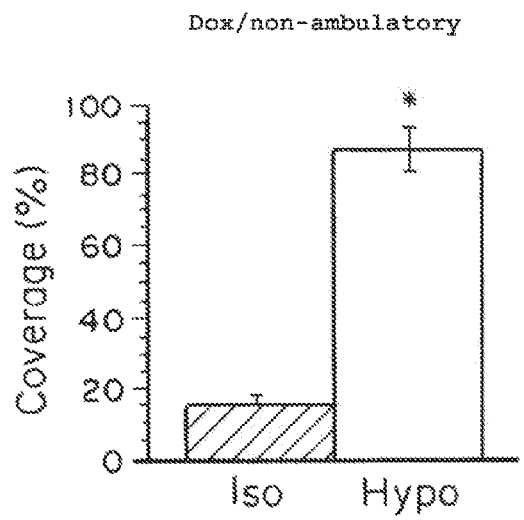
FIGS. 5A and 5B show vaginal coverage by Doxorubicin (Dox) administered in either hypotonic (hypo) or isotonic (iso) solution. Mice (A) remained supine for 1 hr prior to tissue collection (non-ambulatory) or (B) were ambulatory for 10 minutes prior to tissue collection (ambulatory). Images representative of the average vaginal surface coverage for ambulatory mice dosed with Dox in (C) isotonic (iso) and (D) hypotonic (hypo) solution. Data are means±SEM (n=5). *P<0.05 compared to isotonic, Wilcoxon rank-sum test.

When the mice were non-ambulatory (supine for 1 h), only 15% of the vaginal tissue area was covered by Doxorubicin administered in isoosmolar solution, whereas 88% was covered when administered in hypoosmolar solution (FIG. 5A).

Figure 5B:
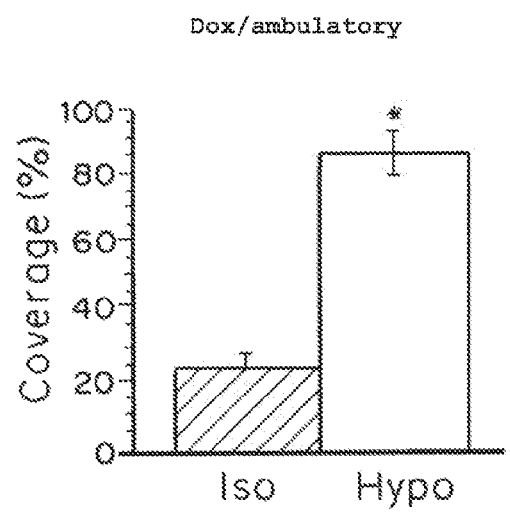

When the mice were ambulatory for 10 mins prior to tissue collection, the isoosmolar solution delivered Doxorubicin to 25% of the vaginal surface area, whereas the hypoosmolar solution delivered it to 86% of the area (FIG. 5B). The isoosmolar solution only delivered the drug to the vaginal surfaces facing the lumen, not the surfaces contained within the collapsed vaginal folds, thus producing the pattern of "stripes" with the unexposed tissue appearing black. In contrast, the hypoosmolar solution distributed the Doxorubicin to the entire vaginal surface.

Effect of Tonicity on Vaginal Drug Retention

Figure 6:
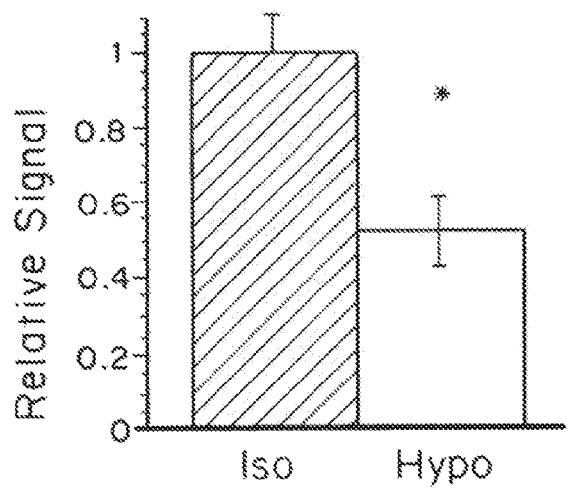
FIG. 6 shows the vaginal retention of Doxorubicin administered in either isotonic (iso) or hypotonic (hypo) solution. Mice remained supine for 10 minutes prior to tissue collection. Overlay of Doxorubicin fluorescence intensity and bright-field images for isotonic solution and hypotonic solution in whole cervicovaginal tract tissue. The relative Doxorubicin signal based on quantification of fluorescent signal, adjusted for solution fluorescence are representative of the averages calculated for n=4 mice and were quantified as relative signal±SEM. *P<0.05 compared to isotonic, Wilxocon rank-sum test.

Isoosmolar and hypoosmolar Doxorubicin solutions were administered intravaginally to anesthetized mice to avoid any effect of solution leakage. After 10 min in the supine position, the entire reproductive tract was excised and analyzed quantitatively with fluorescence imaging. After only 10 min, the relative fluorescent signal of Doxorubicin administered in hypoosmolar solution was half that of Doxorubicin administered in isoosmolar solution (FIG. 6).

Effect of Tonicity on Prevention of Vaginal HSV-2 Infection

The enhanced distribution of hypotonically administered drug was tested at short times and how the reduced retention at longer times would affect the efficacy of a vaginally administered drug. Acyclovir monophosphate (ACVp), a moderately protective drug that provides partial protection when administered 30 min prior to viral inoculum in a mouse model of vaginal HSV-2 infection was used since it would likely reveal any benefit of improved distribution. Similar to Doxorubicin, ACVp is water soluble and acts intracellularly. First, it was ensured that hypotonic fluid did not increase susceptibility to infection by administering the $ID_{50}$ dose of virus (typically infects ~50% of the mice) suspended in either isotonic or hypotonic solution. When virus was administered in either isotonic or hypotonic solution, 60% (9/15) mice were infected. This control experiment indicated changes in infection rate were due to the presence of the drug and not from hypotonic effects on the virus or tissue susceptibility. For protection studies $10ID_{50}$, a dose that typically infects ~90% of the mice, was used.

Figure 7:
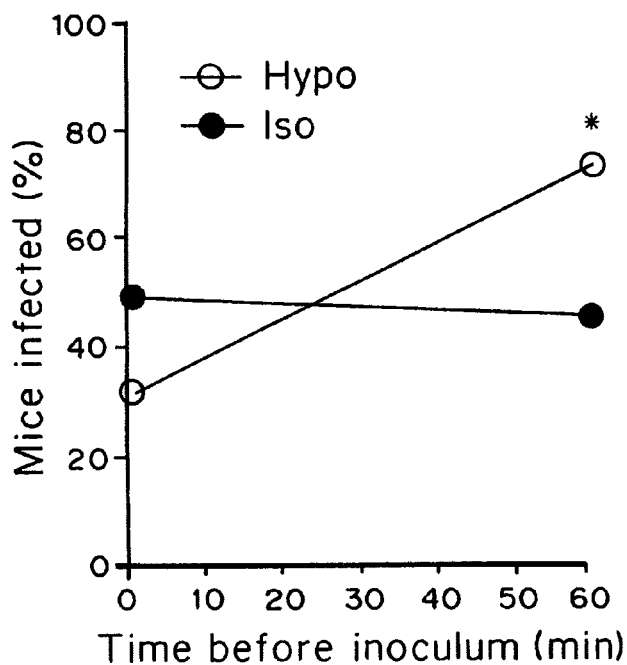
FIG. 7 shows vaginal HSV-2 infection after treatment with acyclovir monophosphate (ACVp) in either hypotonic (hypo) or isotonic (iso) solution. ACVp (10 mg/ml) was administered 1 min or 60 min prior to viral inoculum. n≥45 mice were tested in each group, and infection rates in the control group were ~90%. *P<0.05 compared to isotonic, Fisher's exact test.

When 1% ACVp was administered 1 min before virus, 49% (22/45) of mice were infected when ACVp was administered isotonically, and 31% (14/45) of mice were infected when ACVp was administered hypotonically (FIG. 7). Although this result suggested the hypotonic solution may have increased vaginal protection, this difference was not statistically significant (p=0.1). When 1% ACVp was administered 1 h before virus, 45% (27/60) of mice were infected when ACVp was administered isotonically, and 73% (33/45) of mice were infected when ACVp was administered hypotonically (FIG. 7). This difference was statistically significant, suggesting that although hypotonic delivery may have improved immediate protection, the osmotic flow through the epithelium appeared to remove ACVp from the vagina leading to decreased protection.

Effect of Osmotically-Driven Convection on Vaginal Nanoparticle Distribution

Hypotonic delivery of free drug led to improved distribution in the vaginal tract, but osmotically-induced absorption of fluid may cause drugs for which the vaginal epithelium is permeable to be removed by solvent drag. In contrast, the vaginal epithelium is essentially impermeable to nanoparticles, and, if they are mucus-penetrating, osmotic flow delivers them to the epithelial surface. MPP, capable of penetrating vaginal mucus, coat the entire vaginal surface within 10 min after being delivered in a hypotonic solution. Even if delivered in hypotonic fluid, mucoadhesive nanoparticles (CP) aggregate in the lumenal mucus layers and are not transported through vaginal mucus to the vaginal epithelium by osmotically-induced convection. The dependence on tonicity of osmotically-driven distribution of MPP immediately after administration was determined. By freezing vaginal tissues immediately after MPP administration, one was able to take a "snap-shot" of the initial particle distribution dynamics.

When MPP were administered in isotonic solution, the nanoparticles were found distributed throughout the lumen, but when delivered in hypotonic solutions, a gradient in particle concentration was apparent, with MPP being concentrated at the surface of the vaginal epithelium. From the surface distribution of MPP, it is evident that hypotonically-induced fluid flow resulted in MPP being rapidly drawn to the vaginal surface, without absorption across the epithelium.

Effect of Tonicity on Vaginal Nanoparticle Retention

Figure 8A:
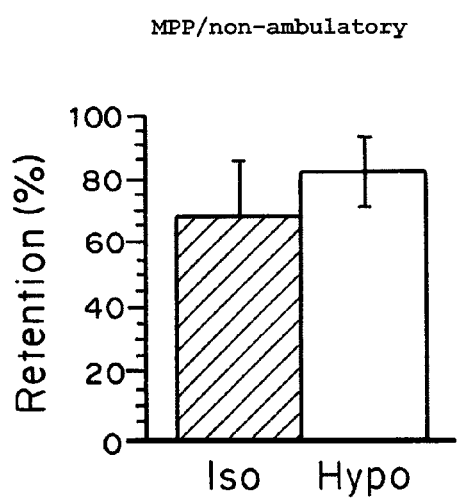
FIGS. 8A and 8B show vaginal retention of MPP administered in either hypotonic (hypo) or isotonic (iso) solution.

It was hypothesized that, in contrast to free dug administered in hypotonic solution, vaginal retention of MPP would improve with hypotonic delivery. Since it was anticipated that fluid leakage would play a role in nanoparticle retention, both non-ambulatory and ambulatory conditions were compared. In the case of non-ambulatory mice (supine for 1 h), 69% of MPP administered in isotonic solution and 83% of MPP administered in hypotonic solution were retained (FIG. 8A). It is likely that the 1 h period allowed for fluid absorption and removed gravitational effects, reducing leakage. Although a higher percentage of MPP were retained when administered in hypotonic solution, the difference was not statistically significant.

Figure 8B:
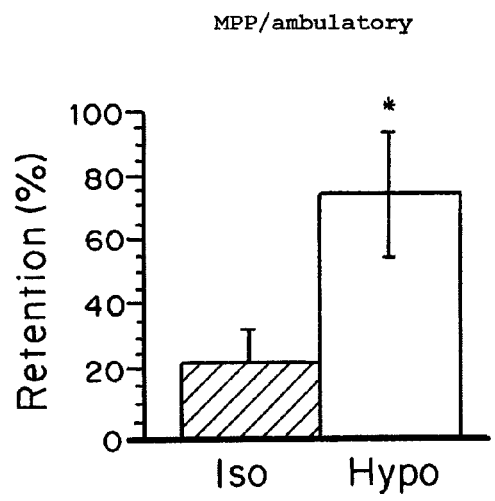

However, when the mice were ambulatory, there was a significant decrease in the retention of MPP administered in isotonic solution. After 10 min of ambulation, only 22% of MPP administered in isotonic solution were retained compared with 75% of MPP administered in hypotonic solution (FIG. 8B). It appears that the rapid delivery of MPP to the vaginal surface led to the increased retention since much of the fluid in the vagina is rapidly discharged during ambulation.

Effect of Osmolality on Vaginal Nanoparticle Distribution

Figure 9:
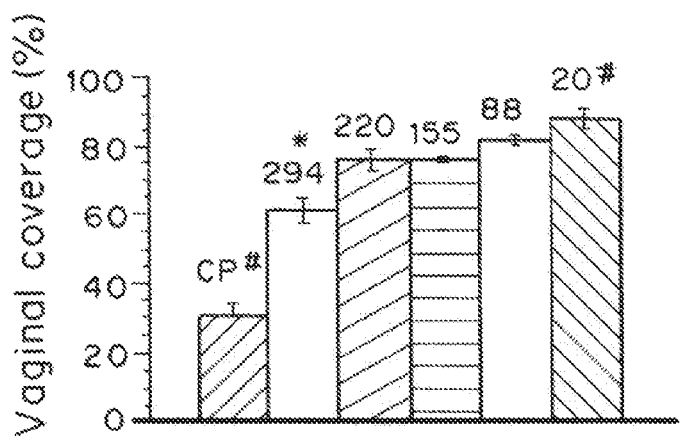
FIG. 9 shows vaginal distribution of fluorescent 100 nm MPPs administered in solutions of varying osmolality in transverse vaginal cryosections and on whole, flattened vaginal tissue. All tissues were collected within 10 min of particle administration. All values have units mOsm/kg. Osmolality for mucoadhesive CP particles was 20 mOsm/kg. Images are representative of n≥5 mice. Data calculated as means±SEM (n≥3). #Reprinted from (4). *P<0.05 as compared to hypotonic solutions (20-220), Wilcoxon rank-sum test.

It is well known that tonicity can strongly affect cells, and recent evidence highlights the toxicity of strongly hypertonic gels on both vaginal and rectal epithelia, particularly with repeated exposure. Hypotonic solutions may also cause toxicity. To avoid potential toxic effects it was investigated whether modest levels of hypotonicity might still improve particle distribution in the vagina. Within 10 min of administration, MPP in hypotonic solutions covering a 10-fold range (20-220 mOsm/kg) delivered MPP to the vaginal surface). In contrast to an isotonic solution (294 mOsm/kg) that left MPP particles distributed throughout the vaginal lumen with few being drawn to the epithelial surface, a modestly hypotonic solution (220 mOsm/kg) caused rapid transport to the epithelial surface. Also, there was a trend toward increase vaginal coverage with increasing hypotonicity: In the most hypotonic solution (20 mOsm/kg), MPP coated 88% of the vaginal epithelium after 10 min, whereas only 60% of the vaginal surface was coated with MPP administered in 294 mOsm/kg solution (FIG. 9). At all tonicities tested, MPP reached a greater fraction of the epithelial surface than muco-adhesive (CP) particles, and the minimally hypotonic solution (220 mOsm/kg) delivered particles to 76% of the vaginal surface, a significant increase compared with 60% coverage by the isotonic solution (294 mOsm/kg).

In conclusion, the studies investigating the use of hypotonic solutions for convection-enhanced drug delivery to the vagina showed that although hypotonic delivery of Doxorubicin improved the vaginal distribution, the drug was absorbed through the epithelium, reducing vaginal retention. In contrast, it was found that hypotonic delivery of mucoinert mucus-penetrating nanoparticles (MPP) improved both distribution and retention. In addition, it was found that even minimally hypotonic delivery significantly improved the vaginal distribution of MPP. The results indicate that hypotonic formulations are more effective for drug delivery to the vagina than the traditional hypertonic formulations, and that MPP delivered hypotonically offer significant promise for non-toxic sustained drug delivery to the entire vaginal surface.

Although there was improved distribution of drug in hypotonic solution, fluid absorption could potentially lead to rapid removal of the drug by fluid transport through the vaginal epithelium. Using acyclovir monophosphate (ACVp), a trend toward improved protection by ACVp in hypotonic solution vaginally administered immediately before HSV-2 virus was demonstrated. The improved protection is likely due to the increase in vaginal coverage by drug administered in hypotonic solution. In contrast, when HSV-2 was administered 1 h after the drug, the protection by ACVp administered in hypotonic solution was significantly decreased compared to ACVp in isotonic solution. Drug absorption across the epithelium with osmotically-induced fluid flow led to drug clearance and decreased protection after 1 h. MPP offer a way to achieve improved distribution of drug by hypotonic delivery since nanoparticles accumulate on the surface of the vaginal epithelium and MPP containing ACVp demonstrated better protection than 10-fold higher concentration of free drug when administered vaginally 30 min prior to HSV-2 virus. MPP are immediately drawn to the vaginal epithelium when administered in a minimally hypotonic solution.

Fluid absorption and secretion can also affect vaginal retention. It was previously demonstrated that in humans that the leakage rate of vaginal gels increased linearly with increasing hypertonicity (Zeitlin et al. *Contraception* 68, 139-155 (2003)). In this case, retention was reduced by osmotically-induced fluid secretion leading to product leakage. This indicates that hypotonic products would cause fluid absorption and reduced leakage, and might thereby improve vaginal retention. It was found that this was not necessarily true for drugs, unlike MPP, that can be absorbed through the vaginal epithelium. MPP, by penetrating into the more slowly cleared mucus layers in the deep vaginal folds, are retained longer than mucoadhesive CP. As shown by this study, MPP are better retained in the vaginal tract of ambulatory mice when administered in hypotonic solution as compared to administration in isotonic solution by reducing vaginal leakage. the results indicate that a hypotonic gel formulation containing MPP would likely enhance both drug distribution and retention in the human vagina.

Example 9

Comparison of Effect of Osmolarity on Particle Uptake in Colon

Materials and Methods

Studies were conducted as described in Examples 7 and 9 comparing distribution of MPP in the mouse colon in solution with varying tonicity. Studies compared particle uptake in the colon with 20 mOsm, 260 mOsm, 350 mOsm, 450 mOsm, 860 mOsm, and 2200 mOsm solutions. The only reason one can obtain advective transport to the epithelium with hyperosmolar solutions is if they were hyperosmolar with Na.

Distribution of various sizes of CP and MPP after rectal coadministration to mice with TNBS-induced colitis was also determined. Fluorescent images of flattened colonic tissue after hypotonic rectal administration of solutions containing a mixture of CP (red) and MPP (green) of various sizes (100 nm, 200 nm, 500 nm) were analyzed. Transverse colonic cryosections of 200 nm CP and MPP (cell nuclei stained blue with DAPI) were also prepared.

Results

The effective osmolality of the colon appears to be between 400-530 mOsm/kg, above blood plasma osmolality (~300 mOsm/kg). This higher range is supported by Billich and Levitan, T Clinical Invest, (1969). Vehicles with an osmolality of 400 mOsm/kg and below provide improved distribution of MPP on the colon tissue surface.

Example 10

Determination of Toxicity of Hypoosmotic MPP Formulations

Recent studies indicate that in response to certain vaginal products, the vaginal epithelium can secrete immune mediators that may enhance susceptibility to sexually transmitted infections. It has also been established that other conditions, such as pre-term labor, are associated with reproductive tract inflammation. Thus, it is important that a vaginal product not induce such an immune response, particularly after repeated dosing. Hyperosmolal formulations previously have been demonstrated as toxic to the vaginal and rectal epithelium, which can negate the protective or therapeutic benefits of administered drugs. Accordingly this study was conducted to insure that hypoosmolal formulations do not cause toxicity when administered to the mucosal epithelium.

Materials and Methods

Seven daily treatments with purely hypotonic (~20 mOsm/kg) fluids (carrying Pluronic F127 or MPPs) and standard isoosmolar hydroxyethylcellulose were compared to no treatment. Hypertonic gel (vehicle containing 20% glycerol, used in clinical trials). A hypotonic gel formulation (HEC gel with 20% increased water content to offset water absorption) containing MPP was compared to a conventional hypertonic gel formulation (HEC containing 20% glycerol, a standard glycerol concentration used for vaginal gel formulations) based on vaginal crosssectional images.

Twenty μL of each test agent was administered intravaginally to the DP mouse model once-a-day for seven days. HEC gel and N9 were provided by T. Moench (Reprotect), and TFV vehicle gel was kindly provided by C. Dezzutti (University of Pittsburgh). On the eighth day, each mouse was lavaged twice with 50 μL of PBS. Each lavage sample was diluted with an additional 200 μL of PBS and centrifuged to remove the mucus plug. Supernatant (200 μL) was removed and split into 50 μL for each of the four (IL-1β, IL-1α, TNF-α, and IL-6) Quantikine ELISA kits (R&D Systems). ELISAs were conducted per the manufacturer's instructions.

Results

Seven daily treatments with purely hypotonic (~20 mOsm/kg) fluids (carrying Pluronic F127 or MPPs) and standard isoosmolar hydroxyethylcellulose do not cause an increase in vaginal cytokines (IL-1 alpha/beta) compared to no treatment. Hypertonic gel (vehicle containing 20% glycerol, used in clinical trials) caused a significant increase in these vaginal cytokines. A hypotonic gel formulation containing MPP was compared to a conventional hypertonic gel formulation based on vaginal crosssectional images. It appears as though the vaginal distribution and retention of MPP after 6 h is improved with the hypotonic (81% retained after 6 h) gel (HEC gel with 20% increased water content to offset water absorption) as compared to the hypertonic (~20% retained after 6 h) gel formulation (HEC containing 20% glycerol, a standard glycerol concentration used for vaginal gel formulations).

We claim:

1. A hypotonic formulation comprising
mucus penetrating particles, the particles comprising;
a mucus penetration enhancing polyalkylene oxide coating which enhances diffusion of the particles through mucus, the coating having a density of polyalkylene oxide equivalent to at least about five 5 kD polyethylene glycol/100 nm² of particle surface or a density of [Γ/Γ*] >1; and
a therapeutic, prophylactic, diagnostic or nutraceutical agent for administration to a mucosal tissue,
in an excipient which is hypotonic for epithelium selected from the group consisting of the eye, gastrointestinal tract, and vagina, the excipient causing water uptake by the epithelium, resulting in the rapid transport of the mucus penetrating particles to the epithelial surface.

2. The formulation of claim 1, wherein the mucus penetrating particles are polymeric nanoparticles comprising a core polymer coated by the polyalkylene oxide mucus penetration enhancing coating.

3. The formulation of claim 2 wherein the mucus penetration enhancing coating is covalently bound to the core polymer.

4. The formulation of claim 1, wherein the mucus-penetrating particles comprise particles comprising the therapeutic, prophylactic, diagnostic or nutraceutical agent.

5. The formulation of claim 1, wherein the mucus penetration enhancing coating material is polyethylene glycol or a block copolymer of polyethylene oxide.

6. The formulation of claim 5, wherein the molecular weight of the polyethylene glycol is between about 1 kD to and about 100 kD and the density of the polyethylene glycol, when measured by 1H NMR, is between about 5 and about 50 5 kD polyethylene glycol chains per 100 nm².

7. The formulation of claim 1, wherein the mucus penetration enhancing coating is present in an amount effective to make the surface charge of the particles neutral or essentially neutral.

8. The formulation of claim 1 for application to the vagina, having an osmolality between 20 and 220 mOsm/kg.

9. The formulation of claim 8 wherein the mucus penetrating nanoparticles comprise a therapeutic agent in an effective amount for vaginal delivery.

10. The formulation of claim 1 for application to the colon or rectum, wherein the osmolality is between about 20 mOsm/kg and 450 mOsm/kg and wherein sodium ions (Na⁺) comprise at least 30% of the osmolality in excess of 220 mOsm/kg.

11. The formulation of claim 10 wherein the mucus penetrating nanoparticles comprise a therapeutic agent in an effective amount for administration to the rectum and/or colon.

12. The formulation of claim 1 selected from the group consisting of solutions, suspensions, gels, ointments, creams, lotions, tablets or capsules, and powders.

13. The formulation of claim 1, wherein the particles provide sustained mucosal delivery of the agent.

14. A method of administering one or more therapeutic, prophylactic, and/or diagnostic agents to a human or animal in need thereof, the method comprising administering an effective amount of the formulation of claim 1 in a manner selected from the group consisting of administration to the vagina, administration to the gastrointestinal tract, administration to the eye or a compartment thereof, administration to the pulmonary tract, intranasal administration, administration to the rectum or colon, sublingual administration, buccal administration, oral administration, topical administration to an ocular area, topical administration to a region of the mouth, topical administration to the rectum, and topical administration to the vagina.

15. The method of claim 14, wherein the formulation is administered enterally.

16. The method of claim 14, wherein the formulation is administered to the eye or to a compartment of the eye.

17. The method of claim 14, wherein the formulation is administered topically to the ocular area, to a region of the mouth, to the vagina, or to the rectum.

18. The method of claim 14, wherein the formulation is applied a compartment of the eye.

19. The method of claim 14, wherein the formulation is administered to the pulmonary tract or intranasally.

20. The method of claim 14, wherein the formulation is administered to the rectum or colon.

21. The method of claim 14, wherein the formulation is administered buccally, sublingually or orally.

* * * * *